United States Patent
Abdi et al.

(10) Patent No.: US 12,326,415 B2
(45) Date of Patent: Jun. 10, 2025

(54) ANTIBODY-FREE RAPID DETECTION OF BACTERIA

(71) Applicants: Yaser Abdi, Tehran (IR); Shahrzad Molavi, Tehran (IR); Ali Bozorg, Tehran (IR)

(72) Inventors: Yaser Abdi, Tehran (IR); Shahrzad Molavi, Tehran (IR); Ali Bozorg, Tehran (IR)

(73) Assignee: University of Tehran (IR)

( * ) Notice: Subject to any disclaimer, the term of this patent is extended or adjusted under 35 U.S.C. 154(b) by 435 days.

(21) Appl. No.: 17/844,341

(22) Filed: Jun. 20, 2022

(65) Prior Publication Data
US 2022/0326176 A1 Oct. 13, 2022

Related U.S. Application Data

(60) Provisional application No. 63/274,015, filed on Nov. 1, 2021.

(51) Int. Cl.
*G01N 27/414* (2006.01)

(52) U.S. Cl.
CPC ..... *G01N 27/4145* (2013.01); *G01N 27/4148* (2013.01)

(58) Field of Classification Search
None
See application file for complete search history.

(56) References Cited

PUBLICATIONS

Karim, et al., "Zinc oxide nanorods-based immune-field-effect transistor for human serum albumin detection", Journal of Material Science, 56: p. 15344-15353, Sep. 2021.*

* cited by examiner

*Primary Examiner* — J. Christopher Ball

(57) ABSTRACT

A method for detecting a species of bacteria in a sample solution. The method includes putting the sample solution in contact with an array of zinc oxide nanorods on a gate region of a field effect transistor (FET) biosensor, applying an alternating current (AC) voltage between source and drain electrodes of the FET biosensor, applying a first direct current (DC) voltage of $V_1$ to the sample solution, measuring a first set of electrical impedance values ($Z_1$) between the source region and the drain region, calculating a first impedance difference set ($\Delta Z_1$) between the $Z_1$ and a respective first initial set of electrical impedance values ($Z_1^0$) associated with a bacteria-free reference solution, determining bacteria indicative factors including a first impedance difference peak value ($\Delta Z_{1m}$) and a respective peak frequency ($f_m$), and detecting a presence of a first species of bacteria in the sample solution based on the bacteria indicative factors.

18 Claims, 26 Drawing Sheets

ANTIBODY-FREE RAPID DETECTION OF BACTERIA

CROSS-REFERENCE TO RELATED APPLICATION

This application claims the benefit of priority from pending U.S. Provisional Patent Application Ser. No. 63/274,015 filed on Nov. 1, 2021, and entitled "SOLUTION-GATED DEVICE FOR BACTERIA DETECTION", which is incorporated herein by reference in its entirety.

TECHNICAL FIELD

The present disclosure generally relates to bacteria detection in a solution, and particularly, to a method and device for antibody-free and label-free detection of bacteria utilizing a solution-gated field effect transistor (FET) biosensor with zinc oxide (ZnO) nanorods as bacteria trapping agents on gate region, and a fabrication process of an exemplary FET biosensor thereof.

BACKGROUND

Timely detection of pathogenic bacteria is important in preventing bacterial contaminations and infections that have always been a major global health threat. Development of rapid and accurate diagnostics methods along with production of drugs is essential to overcoming this problem. Previously reported electrochemical, mechanical and microfluidic sensors and methods using thereof have attempted to meet these requirements.

Current traditional biosensing processes include conventional cell counting methods, polymerase chain reaction (PCR), fluorescent dye labeled probes, and enzyme-linked immunosorbent assay (ELISA). These processes require either time-consuming separation, identification, culturing, counting, and/or sample pretreatment such as cell lysis and DNA extraction, which is an expensive procedure. However, a fundamental trade-off between selectivity and sensitivity of such sensors is still the main challenging and unresolved issue.

Recent advances in electronic devices and biosensors as well as advances in material engineering and nanoscience have provided an opportunity to develop new procedures and methods for rapid detection of bacteria and fabrication of biosensors, such as development of more sensitive methods based on nucleic acid amplification, immuno-assays, fluorescence, microfluidics, nuclear magnetic resonance (NMR), surface plasmon resonance, quartz crystalline microbalance (QCM), surface enhanced Raman spectroscopy as well as various electrochemical methods. Amongst these strategies, electrochemical impedance spectroscopies have proven to be promising for point of care diagnosis, because of their rapid detection and high sensitivity.

Electrochemical cell impedance spectroscopy is used for label-free detection of pathogenic bacteria. It was found that electrical impedance of cell suspensions in solution is resulted from cell wall charges and release of ions or other osmolytes from cells. There are also other approaches that use different signatures of bacteria for detection and identification, such as their effect on the pH value of their solution in ion selective field effect transistors (ISFETs). However, selectivity of previously reported sensors comes from antibody biotinylation and antibody-based methods face severe challenges. For example, no specific antibodies are available for all bacteria and antibodies are often unstable and vulnerable to denaturation. Also, fabrication of such sensors is complicated and expensive.

There is, therefore, a need for a rapid, simple, accurate, and label-free (i.e., antibody and/or enzyme-free) sensing procedure for detecting bacteria in a biological media as well as quantifying an amount of a detected bacteria; thereby, resulting in controlling bacterial disease propagation.

SUMMARY

This summary is intended to provide an overview of the subject matter of the present disclosure, and is not intended to identify essential elements or key elements of the subject matter, nor is it intended to be used to determine the scope of the claimed embodiments. The proper scope of the present disclosure may be ascertained from the claims set forth below in view of the detailed description below and the drawings.

In one general aspect, the present disclosure describes an exemplary method for detecting a species of bacteria in a sample solution. The method may include putting the sample solution in contact with an array of zinc oxide (ZnO) nanorods grown on a gate region of a field effect transistor (FET) biosensor, applying an alternating current (AC) voltage at a set of frequencies of 500 Hz to 2 MHz between a source electrode within a source region of the FET biosensor and a drain electrode within a drain region of the FET biosensor, applying a first direct current (DC) voltage of $V_1$ to the sample solution on the gate region, measuring a first set of electrical impedance values ($Z_1$) between the source region and the drain region responsive to the applied AC voltage and the applied $V_1$, calculating a first impedance difference set ($\Delta Z_1$) by calculating a difference between each electrical impedance value of the $Z_1$ measured at a respective frequency ($f_i$) of the set of frequencies and a respective electrical impedance value of a first initial set of electrical impedance values ($Z_1^0$) associated with a bacteria-free reference solution measured at the same frequency $f_i$, determining bacteria indicative factors, and detecting a presence of a first species of bacteria in the sample solution based on the bacteria indicative factors.

In an exemplary embodiment, the sample solution may include a solution suspected to contain bacteria. In an exemplary embodiment, the $Z_1$ may include a first set of real part magnitude of electrical impedance respective to the set of frequencies.

In an exemplary embodiment, calculating each first impedance difference may be done using a relation defined by the following equation:

$$(\Delta Z_1)f_i = (Z_1)f_i - (Z_1^0)f_i.$$

In an exemplary embodiment, determining the bacteria indicative factors may include detecting a first impedance difference peak value ($\Delta Z_{1m}$) of the $\Delta Z_1$ and determining a peak frequency ($f_m$) of the set of frequencies respective to the $\Delta Z_{1m}$.

In an exemplary embodiment, detecting the presence of the first species of bacteria in the sample solution may include detecting the presence of the first species of bacteria in the sample solution based on at least one of a range of the $\Delta Z_1$, a value of the $f_m$, a value of the $\Delta Z_{1m}$, a sign of a plurality values of the $\Delta Z_1$, and combinations thereof. In an exemplary embodiment, detecting the presence of the first species of bacteria in the sample solution may include detecting a first set of conditions. In an exemplary embodiment, the first set of conditions may include at least one of the calculated $\Delta Z_{1m}$ being within a range of first reference impedance difference peak values ($\Delta Z_{1rm}$) associated with the first species of bacteria, the determined $f_m$ being equal to a reference peak frequency ($f_{rm}$) associated with the first species of bacteria, sign of the plurality values of the $\Delta Z_1$ being the same with sign of a plurality of at least one of first reference impedance difference sets ($\Delta Z_{1r}$) associated with the first species of bacteria, and combinations thereof.

In an exemplary embodiment, determining the $f_m$ may include detecting the $f_m$ equal to a frequency of 1.7 MHz. In an exemplary embodiment, detecting the presence of the first species of bacteria in the sample solution may include detecting a presence of helical bacteria in the sample solution if a constant value for a plurality of the $\Delta Z_1$ respective to a plurality of frequencies more than 1.7 MHz is detected. In another exemplary embodiment, detecting the presence of the first species of bacteria in the sample solution may include detecting a presence of bacteria with longitudinal colonic growth in the sample solution if a negative sign of a plurality values of the $\Delta Z_1$ respective to a plurality of frequencies more than 1.7 MHz is detected. In a further exemplary embodiment, detecting the presence of the first species of bacteria in the sample solution may include detecting a presence of at least one of spherical bacteria with non-longitudinal growth, rod-shaped bacteria with non-longitudinal growth, and combinations thereof in the sample solution if a positive sign of a plurality values of the $\Delta Z_1$ respective to a plurality of frequencies more than 1.7 MHz is detected.

In an exemplary embodiment, the method may further include generating a reference dataset for a plurality of bacteria species. In an exemplary embodiment, generating the reference dataset may include generating a plurality of first reference impedance difference sets ($\Delta Z_{1r}$), a plurality of reference impedance difference peak values ($\Delta Z_{1rm}$) ranges, and a plurality of reference peak frequencies ($f_{rm}$) associated with the plurality of bacteria species. In an exemplary embodiment, generating the reference dataset may include preparing a set of reference solutions containing a respective set of concentrations of each bacteria species of the plurality of the bacteria species and determining the $\Delta Z_{1r}$, the $\Delta Z_{rm}$, and the $f_{rm}$ for each bacteria species.

In an exemplary embodiment, determining the $\Delta Z_{1r}$, the $\Delta Z_{rm}$, and the $f_{rm}$ for each bacteria species may include putting each respective reference solution on the gate region of the FET biosensor in contact with the array of ZnO nanorods, applying the AC voltage with the set of frequencies between the source electrode and the drain electrode while applying the $V_1$ to the gate region, measuring a respective first reference set of electrical impedance values ($Z_{1r}$) including a set of real part magnitude of electrical impedance between the source region and the drain region respective to the set of frequencies, calculating a respective first reference impedance difference set ($\Delta Z_{1r}$), detecting a respective first reference peak value $\Delta Z_{1rm}$ of the first reference impedance difference set $\Delta Z_{1r}$, and determining a reference peak frequency ($f_{rm}$) of the set of frequencies respective to the $\Delta Z_{1rm}$.

In an exemplary embodiment, calculating the first reference impedance difference set ($\Delta Z_{1r}$) may include calculating a difference between each electrical impedance value of the $Z_{1r}$ and a respective electrical impedance value of the first initial set $Z_1^0$ using a relation defined by following equation:

$$(\Delta Z_{1r})f_i = (Z_{1r})f_i - (Z_1^0)f_i.$$

In an exemplary embodiment, the method may further include measuring the first initial set of electrical impedance values ($Z_1^0$). In an exemplary embodiment, measuring the $Z_1^0$ may include putting the bacteria-free reference solution on the gate region of the FET biosensor in contact with the array of ZnO nanorods, applying the AC voltage between the source electrode and the drain electrode at the set of frequencies, applying the first DC voltage of $V_1$ to the bacteria-free reference solution on the gate region, and measuring a set of real part magnitude of electrical impedance between the source region and the drain region versus the set of frequencies.

In an exemplary embodiment, the method may further include measuring a change in impedance difference peak value responsive to a change in the applied DC voltage. In an exemplary embodiment, measuring the change in impedance difference peak value responsive to the change in the applied DC voltage may include applying a second DC voltage of $V_2$ to the sample solution on the gate region, measuring a second set of electrical impedance values ($Z_2$) between the source region and the drain region responsive to the applied AC voltage and the applied $V_2$, calculating a second impedance difference set ($\Delta Z_2$), and determining a second impedance difference peak value ($\Delta Z_{2m}$) of the $\Delta Z_2$ respective to the peak frequency ($f_m$).

In an exemplary embodiment, applying the first DC voltage of $V_1$ to the sample solution may include applying a DC voltage of 1 V to the sample solution. In an exemplary embodiment, applying the second DC voltage of $V_2$ to the sample solution may include applying a DC voltage of 2 V to the sample solution.

In an exemplary embodiment, the $Z_2$ may include a second set of real part magnitude of electrical impedance respective to the set of frequencies. In an exemplary embodiment, calculating the $\Delta Z_2$ may include calculating a difference between each electrical impedance value of the $Z_2$ measured at a respective frequency ($f_i$) of the set of frequencies and a respective electrical impedance value of a second initial set of electrical impedance values ($Z_2^0$) measured at the same frequency $f_i$. In an exemplary embodiment, calculating each second impedance difference may be done using a relation defined by the following equation:

$$(\Delta Z_2)f_i = (Z_2)f_i - (Z_2^0)f_i.$$

In an exemplary embodiment, determining the bacteria indicative factors may further include determining a parameter g as an indicator of the change in impedance difference peak value responsive to the change in the applied DC voltage. In an exemplary embodiment, determining the parameter g may include calculating the parameter g using a relation defined by the following equation:

$$g = \frac{\Delta Z_{2m} - \Delta Z_{1m}}{V_2 - V_1}.$$

In an exemplary embodiment, detecting the presence of the first species of bacteria in the sample solution may further include detecting sign of the parameter g being the same with sign of a reference g ($g_r$) range associated with the first species of bacteria.

In an exemplary embodiment, detecting the presence of the first species of bacteria in the sample solution may include detecting a presence of helical bacteria in the sample solution if a second set of conditions is detected. In an exemplary embodiment, second set of conditions may include the determined $f_m$ being equal to a frequency of 1.7

MHz, a constant value for a plurality of the $\Delta Z_1$ respective to a plurality of frequencies more than 1.7 MHz, and a negative sign of the calculated parameter g.

In an exemplary embodiment, the method may further include measuring the second initial set of electrical impedance values ($Z_2^0$). In an exemplary embodiment, measuring the $Z_2^0$ may include putting the bacteria-free reference solution on the gate region of the FET biosensor in contact with the array of ZnO nanorods, applying the AC voltage between the source electrode and the drain electrode within the set of frequencies, applying the second DC voltage of $V_2$ to the bacteria-free reference solution on the gate region while applying the AC voltage between the source electrode and the drain electrode, and measuring a set of real part magnitude of electrical impedance between the source region and the drain region versus the set of frequencies.

In an exemplary embodiment, generating the reference dataset may further include generating a plurality of reference g ($g_r$) ranges associated with the plurality of bacteria species. In an exemplary embodiment, generating the plurality of $g_r$ ranges may include determining a respective $g_r$ range for each bacteria species. In an exemplary embodiment, determining the respective $g_r$ range for each bacteria species may include putting each respective reference solution on the gate region of the FET biosensor in contact with the array of ZnO nanorods, applying the AC voltage with the set of frequencies between the source electrode and the drain electrode while applying the $V_1$ to the gate region, measuring a respective first reference set of electrical impedance values ($Z_{1r}$) including a first reference set of real part magnitude of electrical impedance between the source region and the drain region respective to the set of frequencies, calculating a respective first reference impedance difference set ($\Delta Z_{1r}$), detecting a respective first reference peak value $\Delta Z_{1rm}$ of the first reference impedance difference set $\Delta Z_{1r}$, determining a reference peak frequency ($f_{rm}$) of the set of frequencies respective to the $\Delta Z_{1rm}$, and measuring a change in reference impedance difference peak value responsive to applying the $V_2$ DC voltage to the gate region.

In an exemplary embodiment, calculating the $\Delta Z_{1r}$ may include calculating a difference between each electrical impedance value of the $Z_{1r}$ and a respective electrical impedance value of the initial set $Z_1^0$ using a relation defined by the following equation:

$$(\Delta Z_{1r})f_i = (Z_{1r})f_i - (Z_1^0)f_i.$$

In an exemplary embodiment, measuring the change in reference impedance difference peak value responsive to applying the $V_2$ DC voltage to the gate region may include calculating a parameter $g_r$ using a relation defined by the following equation:

$$g_r = \frac{\Delta Z_{2rm} - \Delta Z_{1rm}}{V_2 - V_1},$$

Where, the $\Delta Z_{2rm}$ may include a second reference impedance difference peak value at the $f_{rm}$ of a second reference impedance difference set ($\Delta Z_{2r}$) measured responsive to the applied $V_2$.

In an exemplary embodiment, the method may further include determining an amount of the first species of bacteria in the sample solution. In an exemplary embodiment, determining an amount of the first species of bacteria in the sample solution may include determining the amount of the first species of bacteria in the sample solution equal to a $n^{th}$ concentration ($C_n$) of the set of concentrations of the first species of bacteria associated with a first determined $f_{rm}$, a respective $n^{th}$ first reference impedance difference set $(\Delta Z_{1r})_n$, and a respective $n^{th}$ first $g_r$. In an exemplary embodiment, determining the amount of the first species of bacteria in the sample solution equal to the $C_n$ may be done if a third set of conditions is detected. In an exemplary embodiment, the third set of conditions may include the determined $f_m$ being equal to the first determined $f_{rm}$ associated with the first species of bacteria, the calculated $\Delta Z_{1m}$ being equal to a $(\Delta Z_{1rm})_n$ value associated with the $C_n$ of the set of concentrations of the first species of bacteria, and the calculated g being equal to the $n^{th}$ first $g_r$ value associated with the $C_n$ of the set of concentrations of the first species of bacteria. In an exemplary embodiment, determining the amount of the first species of bacteria in the sample solution equal to the $C_n$ may be done if the determined $f_m$ is equal to the first determined $f_{rm}$ associated with the first species of bacteria, the calculated $\Delta Z_{1m}$ is equal to a $(\Delta Z_{1rm})_n$ value associated with the $C_n$ of the set of concentrations of the first species of bacteria, and the calculated g is equal to the $n^{th}$ first $g_r$ value associated with the $C_n$ of the set of concentrations of the first species of bacteria.

In an exemplary embodiment, the method may further include fabricating the FET biosensor. In an exemplary embodiment, fabricating the FET biosensor may include removing impurities from a semiconductor substrate by cleaning the semiconductor substrate, forming a dielectric layer on the semiconductor substrate, forming the source region and the drain region on the semiconductor substrate by patterning and etching the dielectric layer in the source region and the drain region, increasing electrical conductivity of the source region and the drain region via changing semiconductor characteristics of the source region and the drain region by doping the source region and the drain region, growing the array of ZnO nanorods on the gate region on the dielectric layer between the source region and the drain region, and forming the source electrode and the drain electrode by depositing a first electrical conductive layer on the doped source region and a second electrical conductive layer on the doped drain region.

In an exemplary embodiment, the method may further include differentiating a presence of gram-positive bacteria and gram-negative bacteria in the sample solution. In an exemplary embodiment, differentiating the presence of gram-positive bacteria and gram-negative bacteria in the sample solution may include exposing the sample solution on the gate region to blue light irradiation, applying the AC voltage with the set of frequencies of 500 Hz to 2 MHz between the source electrode and the drain electrode, applying the first DC voltage of $V_1$ to the sample solution on the gate region, measuring a third set of electrical impedance values ($Z_3$) between the source region and the drain region responsive to the applied AC voltage and the applied $V_1$ in the presence of blue light radiation, calculating a third impedance difference set ($\Delta Z_3$), detecting a third impedance difference peak value ($\Delta Z_{3m}$) of the $\Delta Z_3$ respective to the peak frequency ($f_m$), and differentiating the presence of gram-positive bacteria and gram-negative bacteria in the sample solution.

In an exemplary embodiment, the $Z_3$ may include a third set of real part magnitude of electrical impedance respective to the set of frequencies.

In an exemplary embodiment, calculating the $\Delta Z_3$ may include calculating a difference between each electrical impedance value of the $Z_3$ measured at a respective frequency ($f_i$) of the set of frequencies and a respective electrical impedance value of the initial set of electrical impedance values ($Z_1^0$) measured at the same frequency $f_i$. In an exemplary embodiment, calculating each third impedance difference may be done using a relation defined by the following equation:

$$(\Delta Z_3)f_i = (Z_3)f_i - (Z_1^0)f_i.$$

In an exemplary embodiment, differentiating the presence of gram-positive bacteria and gram-negative bacteria in the sample solution may include detecting a presence of gram-negative bacteria in the sample solution if the calculated $\Delta Z_{1m}$ and $\Delta Z_{3m}$ have the same sign. In another exemplary embodiment, differentiating the presence of gram-positive bacteria and gram-negative bacteria in the sample solution may include detecting a presence of gram-positive bacteria in the sample solution if the calculated $\Delta Z_{1m}$ and $\Delta Z_{3m}$ have opposite signs.

In another general aspect of the present disclosure, a system for detecting a species of bacteria in a sample solution is described. The system may include a field effect transistor (FET) biosensor, an electrical stimulator-analyzer device, a DC voltage generator, a DC electrode electrically connected to the DC voltage generator, and a processing unit electrically connected to the electrical stimulator-analyzer device and the DC voltage generator.

In an exemplary embodiment, the FET biosensor may include a dielectric layer on surface of a semiconductor substrate except a source region and a drain region, two electrodes including a source electrode on the source region and a drain electrode on the drain region, and an array of zinc oxide (ZnO) nanorods grown on a gate region of the dielectric layer located between the source region and the drain region.

In an exemplary embodiment, the source region and the drain region may include two respective doped parts of the semiconductor substrate. In an exemplary embodiment, the array of ZnO nanorods may be configured to be put in contact with the sample solution placed on the gate region. In an exemplary embodiment, the DC electrode may be configured to be placed inside the sample solution on the gate region.

In an exemplary embodiment, the electrical stimulator-analyzer device may be electrically connected to the two electrodes. In an exemplary embodiment, the electrical stimulator-analyzer device may be configured to apply an alternating current (AC) voltage between the source electrode and the drain electrode and measure an electrical impedance of the FET biosensor between the source region and the drain region.

In an exemplary embodiment, the DC voltage generator may be configured to apply a DC voltage between the source region and the drain region by applying a DC voltage to the gate region utilizing the DC electrode.

In an exemplary embodiment, the processing unit may include a memory having processor-readable instructions stored therein and a processor. In an exemplary embodiment, the processor may be configured to access the memory and execute the processor-readable instructions to configure the processor to perform a method. In an exemplary embodiment, the method may include applying an AC voltage at a set of frequencies of 500 Hz to 2 MHz between the source electrode and the drain electrode utilizing the electrical stimulator-analyzer device, applying a first DC voltage of $V_1$ to the sample solution on the gate region utilizing the DC voltage generator while applying the AC voltage, measuring a first set of electrical impedance values ($Z_1$) between the source region and the drain region responsive to the applied AC voltage and the applied $V_1$ utilizing the electrical stimulator-analyzer device, calculating a first impedance difference set ($\Delta Z_1$), measuring a change in impedance difference peak value responsive to a change in the applied DC voltage, determining bacteria indicative factors, and detecting a presence of a first species of bacteria in the sample solution based on the determined bacteria indicative factors.

In an exemplary embodiment, the $Z_1$ may include a first set of real part magnitude of electrical impedance respective to the set of frequencies.

In an exemplary embodiment, calculating the $\Delta Z_1$ may include calculating a difference between each electrical impedance value of the $Z_1$ measured at a respective frequency ($f_i$) of the set of frequencies and a respective electrical impedance value of a first initial set of electrical impedance values ($Z_1^0$) associated with a bacteria-free reference solution measured at the same frequency $f_i$. In an exemplary embodiment, calculating each first impedance difference being done using a relation defined by the following equation:

$$(\Delta Z_1)f_i = (Z_1)f_i - (Z_1^0)f_i.$$

In an exemplary embodiment, measuring the change in impedance difference peak value responsive to the change in the applied DC voltage may include applying a second DC voltage of $V_2$ to the sample solution on the gate region utilizing the DC voltage generator while applying the AC voltage, measuring a second set of electrical impedance values ($Z_2$) between the source region and the drain region responsive to the applied AC voltage and the applied $V_2$, and calculating a second impedance difference set ($\Delta Z_2$).

In an exemplary embodiment, the $Z_2$ may include a second set of real part magnitude of electrical impedance respective to the set of frequencies.

In an exemplary embodiment, calculating the $\Delta Z_2$ may include calculating a difference between each electrical impedance value of the $Z_2$ measured at a respective frequency ($f_i$) of the set of frequencies and a respective electrical impedance value of a second initial set of electrical impedance values ($Z_2^0$) measured at the same frequency $f_i$. In an exemplary embodiment, calculating each second impedance difference may be done using a relation defined by the following equation:

$$(\Delta Z_2)f_i = (Z_2)f_i - (Z_2^0)f_i.$$

In an exemplary embodiment, determining the bacteria indicative factors may include detecting a first impedance difference peak value ($\Delta Z_{1m}$) of the $\Delta Z_1$, determining a peak frequency ($f_m$) of the set of frequencies respective to the $\Delta Z_{1m}$, and determining a parameter g as an indicator of the change in impedance difference peak value responsive to the change in the applied DC voltage using a relation defined by the following equation:

$$g = \frac{\Delta Z_{2m} - \Delta Z_{1m}}{V_2 - V_1}.$$

In an exemplary embodiment, $\Delta Z_{2m}$ may include a second impedance difference peak value ($\Delta Z_{2m}$) of the $\Delta Z_2$ respective to the determined peak frequency ($f_m$).

In an exemplary embodiment, the method may further include generating a reference dataset for a plurality of bacteria species. In an exemplary embodiment, generating the reference dataset may include generating a plurality of first reference impedance difference sets ($\Delta Z_{1r}$), a plurality of first reference impedance difference peak values ($\Delta Z_{1rm}$) ranges, a plurality of reference g ($g_r$) ranges, and a plurality of a reference peak frequencies ($f_{rm}$) associated with the plurality of bacteria species. In an exemplary embodiment, generating the reference dataset may include preparing a set of reference solutions containing a respective set of concentrations of each bacteria species of the plurality of the bacteria species and determining $\Delta Z_{1r}$, $\Delta Z_{1rm}$, $g_r$ range, and $f_{rm}$ for each bacteria species.

In an exemplary embodiment, determining $\Delta Z_{1r}$, $\Delta Z_{1rm}$, $g_r$ range, and $f_{rm}$ for each bacteria species may include putting each respective reference solution on the gate region of the FET biosensor in contact with the array of ZnO nanorods, applying the AC voltage with the set of frequencies between the source electrode and the drain electrode utilizing the electrical stimulator-analyzer device while applying the $V_1$ to the gate region utilizing the DC voltage generator, measuring a respective first reference set of electrical impedance values ($Z_{1r}$) comprising a first reference set of real part magnitude of electrical impedance between the source region and the drain region respective to the set of frequencies utilizing the electrical stimulator-analyzer device, calculating a respective first reference impedance difference set ($\Delta Z_{1r}$), detecting a respective first reference peak value $\Delta Z_{1rm}$ of the first reference impedance difference set $\Delta Z_{1r}$, determining a reference peak frequency ($f_{rm}$) of the set of frequencies respective to the $\Delta Z_{1rm}$, and measuring a change in reference impedance difference peak value utilizing the electrical stimulator-analyzer device responsive to applying the $V_2$ DC voltage to the gate region.

In an exemplary embodiment, calculating the $\Delta Z_{1r}$ may include calculating a difference between each electrical impedance value of the $Z_{1r}$ and a respective electrical impedance value of the initial set $Z_1^0$ using a relation defined by the following equation:

$$(\Delta Z_{1r})f_r = (Z_{1r})f_r - (Z_1^0)f_r.$$

In an exemplary embodiment, measuring the change in reference impedance difference peak value responsive to applying the $V_2$ DC voltage to the gate region may include calculating a parameter $g_r$ using a relation defined by the following equation:

$$g_r = \frac{\Delta Z_{2rm} - \Delta Z_{1rm}}{V_2 - V_1},$$

Where, the $\Delta Z_{2rm}$ may include a second reference impedance difference peak value at the $f_{rm}$ of a second reference impedance difference set ($\Delta Z_{2r}$) measured responsive to the applied $V_2$.

In an exemplary embodiment, the method may further include measuring $Z_1^0$ and $Z_2^0$. In an exemplary embodiment, measuring $Z_1^0$ and $Z_2^0$ may include putting the bacteria-free reference solution on the gate region of the FET biosensor in contact with the array of ZnO nanorods, applying the AC voltage between the source electrode and the drain electrode within the set of frequencies utilizing the electrical stimulator-analyzer device while applying the $V_1$ utilizing the DC voltage generator to the bacteria-free reference solution on the gate region, measuring a first initial set of real part magnitude of electrical impedance between the source region and the drain region versus the set of frequencies, applying the AC voltage between the source electrode and the drain electrode within the set of frequencies utilizing the electrical stimulator-analyzer device while applying the $V_2$ utilizing the DC voltage generator to the bacteria-free reference solution on the gate region, and measuring a second initial set of real part magnitude of electrical impedance between the source region and the drain region versus the set of frequencies.

In an exemplary embodiment, detecting the presence of the first species of bacteria in the sample solution may include detecting the presence of the first species of bacteria in the sample solution based on at least one of a range of the $\Delta Z_1$, a value of the $f_m$, a value of the $\Delta Z_{1m}$, a sign of a plurality values of the $\Delta Z_1$, a sign of the parameter g, and combinations thereof. In an exemplary embodiment, detecting the presence of the first species of bacteria in the sample solution may include detecting the calculated $\Delta Z_{1m}$ is within a range of first reference impedance difference peak values ($\Delta Z_{1rm}$) associated with the first species of bacteria. In an exemplary embodiment, detecting the presence of the first species of bacteria in the sample solution may further include detecting the determined $f_m$ is equal to a reference peak frequency ($f_{rm}$) associated with the first species of bacteria. In an exemplary embodiment, detecting the presence of the first species of bacteria in the sample solution may additionally include detecting sign of the plurality values of the $\Delta Z_1$ is the same with sign of a plurality of at least one of first reference impedance difference sets ($\Delta Z_{1r}$) associated with the first species of bacteria. Furthermore, detecting the presence of the first species of bacteria in the sample solution may include detecting sign of the parameter g is the same with sign of a reference g ($g_r$) range associated with the first species of bacteria.

BRIEF DESCRIPTION OF THE DRAWINGS

The drawing figures depict one or more embodiments in accord with the present teachings, by way of example only, not by way of limitation. In the figures, like reference numerals refer to the same or similar elements.

DETAILED DESCRIPTION

Figure 1:
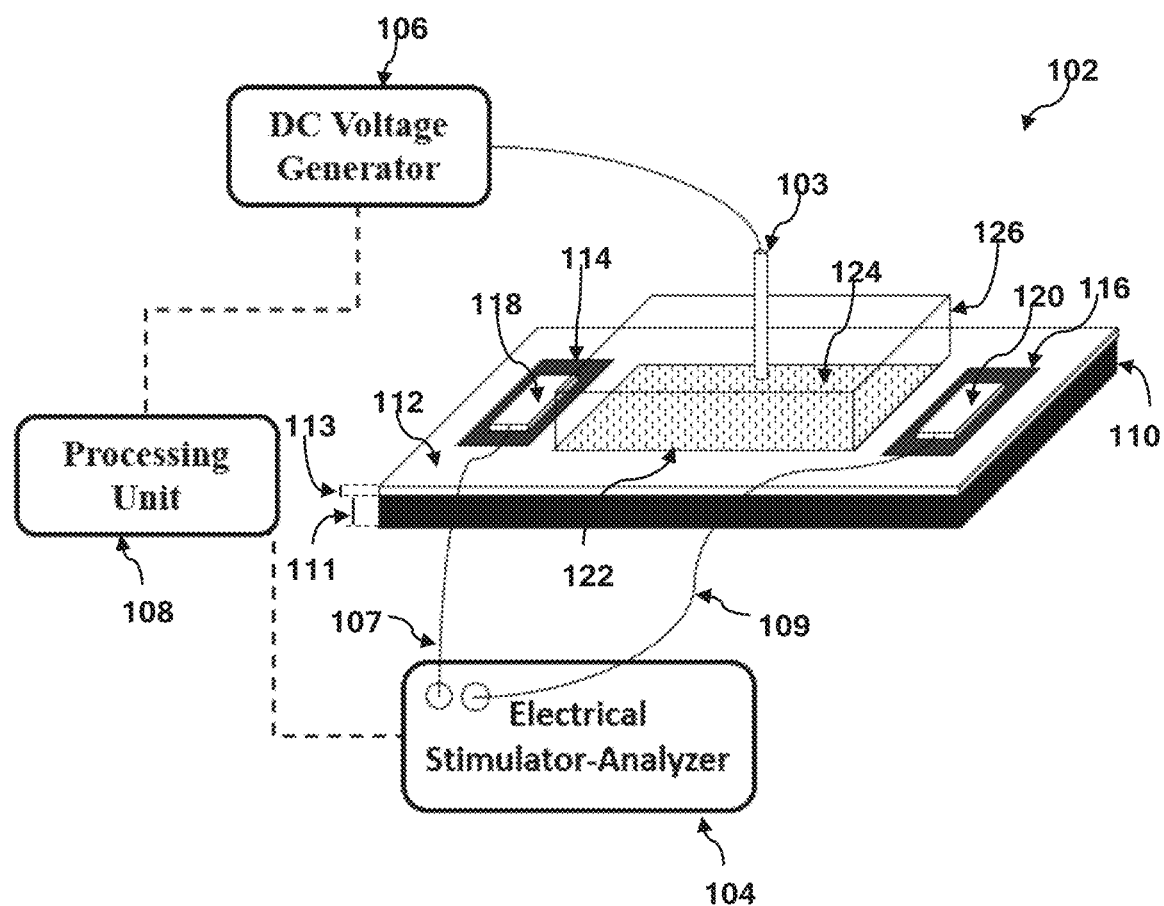
FIG. 1 shows a schematic view of an exemplary system for detecting a species of bacteria in a sample, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary embodiments will be readily apparent to one skilled in the art, and the general principles defined herein may be applied to other embodiments and applications without departing from the scope of the present disclosure. The present disclosure is not intended to be limited to the embodiments shown, but is to be accorded the widest possible scope consistent with the principles and features disclosed herein.

Herein, an exemplary label-free and antibody-free device, system, and method capable of sensitive and selective detection of bacteria is described. An exemplary device, system, and method may provide a fingerprint for any type of bacteria since each type of bacteria may induce unique electrical characteristics on an exemplary device/system according to shape and electrostatic properties of an exemplary type of bacteria. Exemplary induced electrical characteristics may be measured and analyzed utilizing an exemplary method, device, and system to detect type and amount of an exemplary bacteria, so that selectively detection of an exemplary bacteria may be achieved. In an exemplary embodiment, an exemplary biosensor with capability of rapid detection of different bacteria without needing bacteria bio-receptors may be fabricated and utilized for antibody-free detection of bacteria based on unique electrostatic properties of each bacteria species by defining some frequency dependent electronic parameters to selectively detect bacteria species.

In an exemplary embodiment, an exemplary device may include an exemplary field effect transistor (FET) biosensor with zinc oxide (ZnO) nanorods as bacteria trapping agents on an exemplary gate region of an exemplary FET biosensor. An exemplary FET biosensor may include a solution-gated transistor with gold (Au) source and drain electrodes and a gate region in the middle of exemplary source and drain electrodes covered with a layer of ZnO nanorods thereon without needing to antibodies/bacteria markers.

In an exemplary embodiment, an exemplary FET biosensor may be used for detecting a species of bacteria in a sample solution. An exemplary sample solution may be dropped on an exemplary gate region of an exemplary FET biosensor. In an exemplary embodiment, exemplary ZnO nanorods grown on an exemplary transistor gate cannel of an exemplary FET biosensor may provide an effective adhesion of a large number of bacteria/cells in an exemplary sample solution to an exemplary gate region and consequently a sensitivity of an exemplary FET biosensor for detection of bacteria in an exemplary sample solution may be increased. It should be noted that ZnO is a semiconductor material with a direct band gap (3.34 ev), high electrical conductivity, and a large surface area. An isoelectric point (IEP) of ZnO is around 9.7, meaning that in an environment with a pH less than its IEP, an electrical double layer is created that makes a surface of ZnO positively charged. Accordingly, ZnO may be a suitable material for immobilizing molecules with lower IEP, such as DNA, protein, and enzyme. Because of having a large surface area, low-cost synthesizing methods, and good adhesion to biomolecules, ZnO may be an attractive material in biosensor fabrications.

In an exemplary embodiment of the present disclosure, an exemplary system for detecting exemplary species of bacteria in an exemplary sample solution may be described. In an exemplary embodiment, an exemplary system may include an exemplary FET biosensor, an electrical stimulator-analyzer device electrically connected to source-drain electrodes of an exemplary FET biosensor, a direct current (DC) electrode configured to be placed inside an exemplary sample solution within an exemplary gate region of an exemplary FET biosensor, a DC voltage generator configured to apply a DC voltage between an exemplary source region and an exemplary drain region by applying a DC voltage to an exemplary gate region utilizing an exemplary DC electrode, and a processing unit electrically connected to an exemplary electrical stimulator-analyzer device and an exemplary DC voltage generator.

In an exemplary method, utilizing an exemplary system, a suspected solution that is suspected to have bacteria therein may be placed on an exemplary gate region in contact with exemplary ZnO nanorods. An exemplary Ag/AgCl reference electrode may be placed within an exemplary suspected solution in an exemplary gate region. An exemplary Ag/AgCl reference electrode may be configured to apply a DC voltage to an exemplary gate region with an exemplary suspected solution thereon using an exemplary DC voltage generator device. A source-drain current of an exemplary FET biosensor may be monitored under AC bias voltage with different frequencies from 500 Hz to 2 MHz. Additionally, having a three-electrode device as a sensor, including an exemplary reference electrode in an exemplary gate region for applying a DC voltage and a set of a source-drain electrodes for applying an AC voltage, may provide an advantage of investigating bacteria's behavior under two simultaneously varying parameters (i.e., AC voltage with a set of varying frequencies and DC voltage). Thereby, high accurate bacteria detection may be achieved. In an exemplary method, a set of source-drain electrical impedance values of an exemplary FET biosensor may be monitored at a respective set of frequencies of an exemplary applied AC voltage in the presence of an exemplary sample solution on an exemplary gate region while applying an exemplary DC voltage to an exemplary gate region. In an exemplary method, a peak impedance value of an exemplary monitored set of electrical impedance values and a frequency of an exemplary set of frequencies respective to an exemplary peak impedance value may be bacteria indicative factors utilized for identifying species and amount of an exemplary bacteria in an exemplary sample solution. In addition, an effect of varying an exemplary DC voltage applied to an exemplary gate region on an exemplary peak impedance value may be measured as an additional bacteria indicative factor utilized for more accurate and selective identification of species and amount of an exemplary bacteria in an exemplary sample solution. An exemplary method may benefit from advantage of impedance spectroscopy but without a need to antibodies or enzymes as bacteria markers. An exemplary measured peak impedance may depend on shape and surface charges of bacteria so that an exemplary peak impedance, a respective peak frequency, and peak impedance changes in response to changes in gate DC voltage may be used as bacteria indicative parameters utilizing an exemplary method and system herein.

FIG. 1 shows a schematic view of an exemplary system 100 for detecting a species of bacteria in a sample, consistent with one or more exemplary embodiments of the present disclosure. Exemplary system 100 may include an exemplary field effect transistor (FET) biosensor 102, an exemplary electrical stimulator-analyzer device 104 electrically connected to two exemplary electrodes 118 and 120 of FET biosensor 102, an exemplary DC voltage generator 106, an exemplary direct current (DC) electrode 103 connected to DC voltage generator 106, and a processing unit 108 electrically connected to electrical stimulator-analyzer device 104 and DC voltage generator 106.

In an exemplary embodiment, FET biosensor 102 may include an exemplary semiconductor substrate 110, an exemplary dielectric layer 112 coated on parts of surface of semiconductor substrate 110, an exemplary source region 114 of semiconductor substrate 110, an exemplary drain region 116 of semiconductor substrate 110, two exemplary electrodes 118 and 120 including an exemplary source electrode 118 placed on source region 114 and an exemplary drain electrode 120 placed on drain region 116, an exemplary gate region 122 of dielectric layer 112 located between source region 114 and drain region 116, and an exemplary array of zinc oxide (ZnO) nanorods 124 grown on gate region 122.

In an exemplary embodiment, semiconductor substrate 110 may include a silicon wafer with a thickness 111 in a range of about 300 μm to about 500 μm. In an exemplary embodiment, dielectric layer 112 may be coated on surface of semiconductor substrate 110 except source region 114 and drain region 116. In an exemplary embodiment, dielectric layer 112 may include a layer of silicon dioxide ($SiO_2$) grown on parts of surface of semiconductor substrate 110 except a surface of source region 114 and a surface drain region 116. In an exemplary embodiment, dielectric layer 112 may have a thickness 113 in a range of about 50 nm to about 300 nm.

In an exemplary embodiment, source region 114 and drain region 116 may include two respective doped parts of semiconductor substrate 110. In an exemplary embodiment, source region 114 and drain region 116 may include comprise of two respective doped parts of semiconductor substrate 110 with at least one of phosphorus (P), arsenic (As), antimony (Sb), boron (B), and indium (In).

In an exemplary embodiment, two electrodes 118 and 120 may include an exemplary source electrode 118 placed on source region 114 and an exemplary drain electrode 120 on drain region 116. In an exemplary embodiment, source electrode 118 may include a first gold (Au) layer with a thickness in a range of about 100 nm to about 200 nm deposited on source region 114. In an exemplary embodiment, drain electrode 120 may include a second gold (Au) layer with a thickness in a range of about 100 nm to about 200 nm deposited on drain region 116.

In an exemplary embodiment, gate region 122 may include a part of dielectric layer 112 located between source region 114 and drain region 116. In an exemplary embodiment, an exemplary array of zinc oxide (ZnO) nanorods 124 may be grown on a top surface of gate region 122. In an exemplary embodiment, array of ZnO nanorods 124 may cover surface of gate region 122. In an exemplary embodiment, array of ZnO nanorods 124 may include a plurality of ZnO nanorods each with a diameter in a range of about 50 nm to about 200 nm and a length in a range of about 3 μm to about 10 μm.

In an exemplary embodiment, FET biosensor 102 may be configured to put an exemplary sample solution thereon. In an exemplary embodiment, gate region 122 may be configured to put an exemplary sample solution thereon. In an exemplary embodiment, array of ZnO nanorods 124 may be configured to be in contact with an exemplary sample solution placed on gate region 122.

In an exemplary embodiment, array of ZnO nanorods 124 may be bioreceptors for detecting bacteria cells in an exemplary sample solution; allowing for a label-free and antibody-free sensing of bacteria. An isoelectric point (IEP) of ZnO may be high enough that ZnO surface becomes positively charged in a bacteria culturing solution with a pH of about 7. Moreover, a bacteria cell surface has a negatively net charge because of carboxylate, amino, and phosphate groups. Therefore, array of ZnO nanorods 124 with positively charged surface may facilitate adhesion of negatively charged bacteria cells to exemplary gate region 122 by capturing bacteria cells. Bacteria adhesion to surface of gate region 122 may change surface capacitance and impedance while applying an AC voltage between source region 114 and drain region 116.

In an exemplary embodiment, FET biosensor 102 may further include an exemplary container 126 with two open sides placed around gate region 122. In an exemplary embodiment, container 126 may include a cubic container with an open top side and an open bottom side. In an exemplary embodiment, container 126 may be configured to surround gate region 122 with ZnO nanorods 124 thereon, load an exemplary sample solution therein, keep an exemplary sample solution there inside on gate region 122 and in contact with array of ZnO nanorods 124, and prevent a penetration of an exemplary sample solution from gate region 122 towards source electrode 118 and/or drain electrode 120.

In an exemplary embodiment, an exemplary sample solution may refer to a solution that is suspected to contain bacteria. In an exemplary embodiment, an exemplary sample solution may include a sample drawn from a living body, for example, a human or an animal. In an exemplary embodiment, an exemplary sample solution may include a blood sample or a sputum sample drawn from an exemplary living body.

In an exemplary embodiment, electrical stimulator-analyzer device 104 may be electrically connected to two exemplary electrodes 118 and 120 of FET biosensor 102. In an exemplary embodiment, electrical stimulator-analyzer device 104 may be electrically connected to source electrode 118 via an exemplary electrically conductive line 107. In an exemplary embodiment, electrical stimulator-analyzer device 104 may be electrically connected to drain electrode 120 via an exemplary electrically conductive line 109. In an exemplary embodiment, electrical stimulator-analyzer device 104 may be further electrically connected to processing unit 108. In an exemplary embodiment, electrical stimulator-analyzer device 104 may be configured to apply an alternating current (AC) voltage between source electrode 118 and drain electrode 120 and measure an electrical response from FET biosensor 102 responsive to an exemplary AC voltage being applied between source electrode 118 and drain electrode 120. In an exemplary embodiment, electrical stimulator-analyzer device 104 may be configured to measure an electrical impedance between source electrode 118 and drain electrode 120 responsive to an exemplary AC voltage being applied between source electrode 118 and drain electrode 120.

In an exemplary embodiment, DC voltage generator 106 may be configured to apply a DC voltage between source region 114 and drain region 116 by applying a DC voltage to an exemplary solution placed on gate region 122. In an exemplary embodiment, DC voltage generator 106 may be configured to apply an exemplary DC voltage to an exemplary solution (not illustrated), placed on gate region 122, utilizing exemplary DC electrode 103. In an exemplary embodiment, DC electrode 103 may be configured to be placed inside an exemplary solution located on gate region 122. Furthermore, DC electrode 103 may be connected to DC voltage generator 106. In an exemplary embodiment, DC electrode 103 may include a silver chloride electrode (Ag/AgCl electrode).

In an exemplary embodiment, processing unit 108 may be electrically connected to electrical stimulator-analyzer device 104 and DC voltage generator 106 via wireless electrical connections (not illustrated) or utilizing two respective electrically conductive lines (not illustrated). In an exemplary embodiment, processing unit 108 may be electrically connected to electrical stimulator-analyzer device 104 and DC voltage generator 106 via wireless electrical connections utilizing Bluetooth modules embedded in processing unit 108, electrical stimulator-analyzer device 104, and DC voltage generator 106.

In an exemplary embodiment, processing unit 108 may include a memory having processor-readable instructions stored therein and a processor. An exemplary processor may be configured to access the memory and execute the processor-readable instructions. In an exemplary embodiment, the processor may be configured to perform a method by executing the processor-readable instructions. In an exemplary embodiment, an exemplary method may include an exemplary method described herein below for detecting a species of bacteria in an exemplary sample solution suspected to contain bacteria therein.

Figure 2A:
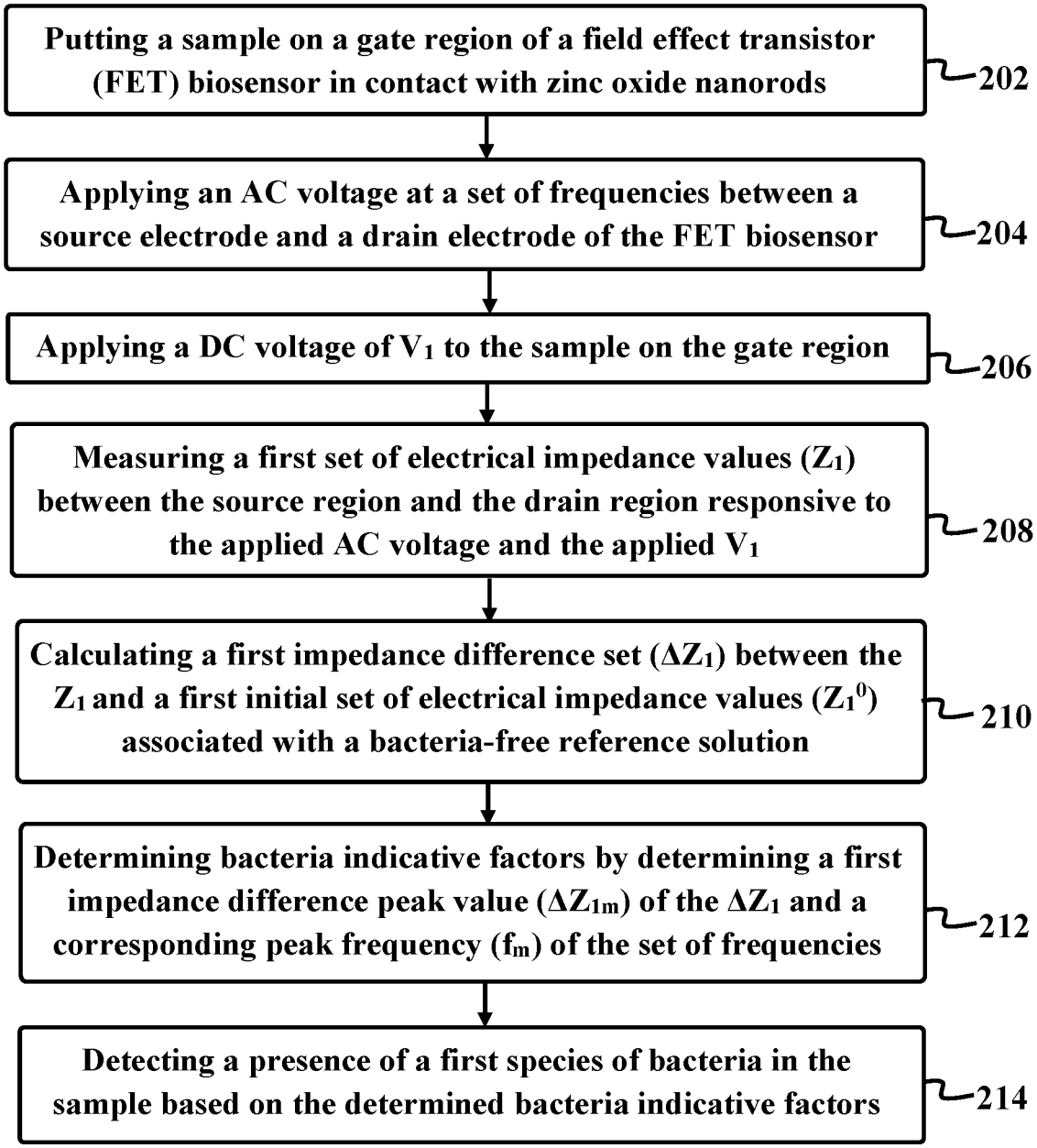
FIG. 2A shows a flowchart of an exemplary method for detecting a species of bacteria in a sample, consistent with one or more exemplary embodiments of the present disclosure.

In an exemplary embodiment, the present disclosure describes an exemplary method for detecting an exemplary species of bacteria in an exemplary sample solution. FIG. 2A shows a flowchart of an exemplary method 200 for detecting an exemplary species of bacteria in an exemplary sample solution, consistent with one or more exemplary embodiments of the present disclosure. Exemplary method 200 may include putting a sample solution in contact with an array of zinc oxide (ZnO) nanorods grown on a gate region of an exemplary field effect transistor (FET) biosensor (step 202), applying an alternating current (AC) voltage at a set of frequencies between a source electrode of the FET biosensor and a drain electrode of the FET biosensor (step 204), applying a first direct current (DC) voltage to the sample solution on the gate region (step 206), measuring a first set of electrical impedance values ($Z_1$) between a source region and a drain region of the FET biosensor responsive to the applied AC voltage and the applied $V_1$ (step 208), calculating a first impedance difference set ($\Delta Z_1$) between the $Z_1$ and a first initial set of electrical impedance values ($Z_1^0$) associated with a bacteria-free reference solution (step 210), determining bacteria indicative factors (step 212), and detecting a presence of a first species of bacteria in the sample solution based on the determined bacteria indicative factors (step 214).

In further detail with respect to step 202, putting an exemplary sample solution in contact with an exemplary array of ZnO nanorods grown on an exemplary gate region of an exemplary FET biosensor (step 202) may include putting an exemplary sample solution in contact with array of ZnO nanorods 124 of FET biosensor 102. In an exemplary embodiment, putting an exemplary sample solution in contact with array of ZnO nanorods 124 of FET biosensor 102 may include placing an exemplary sample solution inside container 126 on gate region 122 and in contact with array of ZnO nanorods 124.

In further detail with respect to step 204, step 204 may include applying an AC voltage at a set of frequencies between an exemplary source electrode of an exemplary FET biosensor and an exemplary drain electrode of an exemplary FET biosensor. In an exemplary embodiment, step 204 may include applying an AC voltage at a set of frequencies in a range of about 500 Hz to about 2 MHz between exemplary source electrode 118 within source region 114 and exemplary drain electrode 120 within drain region 116 of FET biosensor 102. In an exemplary embodiment, applying the AC voltage at the set of frequencies may be performed utilizing electrical stimulator-analyzer device 104.

In further detail with respect to step 206, step 206 may include applying a first DC voltage of $V_1$ to an exemplary sample solution placed within an exemplary gate region of an exemplary FET biosensor. In an exemplary embodiment, applying the first DC voltage of $V_1$ to an exemplary sample solution placed within an exemplary gate region may include applying the first DC voltage of $V_1$ to an exemplary sample solution placed on gate region 122 using DC voltage generator 106 and DC electrode 103. In an exemplary embodiment, the $V_1$ may be applied by DC voltage generator 106 to DC electrode 103 placed inside an exemplary sample solution on gate region 122.

In further detail with respect to step 208, step 208 may include measuring a first set of electrical impedance values ($Z_1$) between an exemplary source region and an exemplary drain region of an exemplary FET biosensor responsive to the applied AC voltage between an exemplary source electrode and an exemplary drain electrode and the applied $V_1$ to an exemplary sample solution in an exemplary gate region. In an exemplary embodiment, step 208 may include measuring the first set of electrical impedance values ($Z_1$) between source region 114 and the drain region 116 of FET biosensor 102 responsive to an exemplary applied AC voltage between source electrode 118 and drain electrode 120, and an exemplary applied $V_1$ to an exemplary sample solution on gate region 122. In an exemplary embodiment, an exemplary $Z_1$ may include a first set of real part magnitude of electrical impedance between source region 114 and the drain region 116 measured respective to the set of frequencies electrical stimulator-analyzer device 104.

In further detail with respect to step 210, step 210 may include calculating a first impedance difference set ($\Delta Z_1$) between the $Z_1$ and a first initial set of electrical impedance values ($Z_1^0$) associated with a bacteria-free reference solution. In an exemplary embodiment, calculating the first impedance difference set ($\Delta Z_1$) may include calculating a difference between each electrical impedance value of the $Z_1$ measured at a respective frequency ($f_i$) of the set of frequencies and a respective electrical impedance value of the $Z_1^0$ measured at the same frequency $f_i$. In an exemplary embodiment, calculating each first impedance difference may be performed using a relation defined by Equation 1:

$$(\Delta Z_1) f_i = (Z_1) f_i - (Z_1^0) f_i \qquad \text{Equation 1}$$

Where, $(Z_1)f_i$ is an electrical impedance value of the $Z_1$ measured at a respective frequency ($f_i$) of the set of frequencies, $(Z_1^0)f_i$ is an electrical impedance value of the $Z_1^0$ measured at the same frequency ($f_i$), and $(\Delta Z_1)f_i$ is a value of the first impedance difference set ($\Delta Z_1$) respective to the $(Z_1)f_i$ and $(Z_1^0)f_i$.

In an exemplary embodiment, the $Z_1^0$ may include a first initial set of electrical impedance values between source region 114 and the drain region 116 of FET biosensor 102 measured via a process including similar to a process of steps 202-208 of exemplary method 200. In an exemplary embodiment, exemplary method 200 may further include measuring the first initial set of electrical impedance values ($Z_1^0$). In an exemplary embodiment, measuring the $Z_1^0$ may include putting a bacteria-free reference solution on gate region 122 of FET biosensor 102 in contact with array of ZnO nanorods 124, applying an AC voltage between source electrode 118 and drain electrode 120 at the set of frequencies in a range of about 500 Hz to about 2 MHz, applying the $V_1$ utilizing DC voltage generator 106 and DC electrode 103 to the bacteria-free reference solution on gate region 122, and measuring a set of real part magnitude of electrical impedance between source region 114 and the drain region 116 versus the set of frequencies.

In further detail with respect to step 212, step 212 may include determining bacteria indicative factors. In an exemplary embodiment, determining bacteria indicative factors may include detecting two parameters as indicators of presence of bacteria in the sample solution. In an exemplary embodiment, the two parameters may include a peak value ($\Delta Z_{1m}$) of the $\Delta Z_1$ and a respective frequency value to the $\Delta Z_{1m}$ within the set of frequencies in the range of about 500 Hz to about 2 MHz. In an exemplary embodiment, $\Delta Z_{1m}$ may include a maximum value among first impedance difference values of the first impedance difference set ($\Delta Z_1$). In an exemplary embodiment, step 212 may include detecting the first impedance difference peak value ($\Delta Z_{1m}$) of the $\Delta Z_1$ and determining a peak frequency ($f_m$) of the set of frequencies respective to the $\Delta Z_{1m}$. In an exemplary embodiment, step 212 may be performed utilizing processing unit 108.

In further detail with respect to step 214, step 214 may include detecting a presence of a first species of bacteria in the sample solution based on the determined bacteria indicative factors. In an exemplary embodiment, detecting the presence of the first species of bacteria in the sample solution may be performed based on at least one of the measured $\Delta Z_1$, the detected $f_m$, the detected $\Delta Z_{1m}$, and combinations thereof. In an exemplary embodiment, detecting the presence of the first species of bacteria in the sample solution may be performed based on at least one of a range of the $\Delta Z_1$, a value of the $f_m$, a value of the $\Delta Z_{1m}$, a sign of a plurality values of the $\Delta Z_1$, and combinations thereof. In an exemplary embodiment, detecting the presence of the first species of bacteria in the sample solution may be performed utilizing processing unit 108.

In an exemplary embodiment, detecting the presence of the first species of bacteria in the sample solution may include detecting at least one of a type of bacteria, a shape of bacteria, a concentration of bacteria, and combinations thereof in the sample solution. In an exemplary embodiment, detecting the presence of the first species of bacteria in the sample solution may include detecting a presence of at least one of helical bacteria, spherical bacteria, rod-shaped bacteria, bacteria with longitudinal colonic growth, bacteria with non-longitudinal growth, bacteria with non-longitudinal growth, gram-positive bacteria, gram-negative bacteria, and combinations thereof.

Figure 2B:
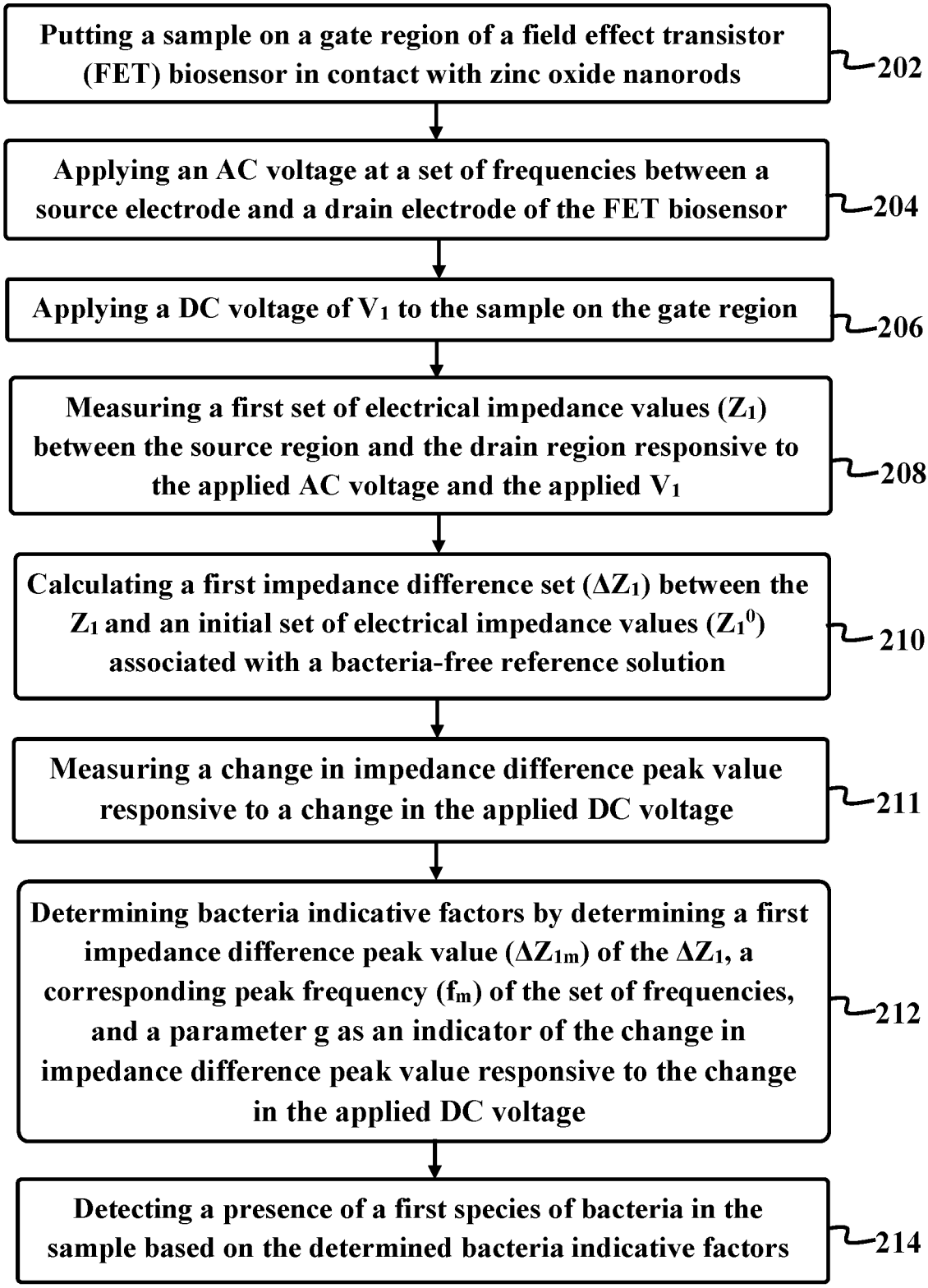
FIG. 2B shows a flowchart of another exemplary method for detecting a species of bacteria in a sample, consistent with one or more exemplary embodiments of the present disclosure.

In exemplary method 200, more bacteria indicative factors may be determined in step 212 and may be utilized in step 214 for detecting the presence of the first species of bacteria in the sample solution. In another embodiment, an exemplary method 220 may contain all the steps of method 200 in addition to step 211 which may entail measuring a change in impedance difference peak value responsive to a change in the applied DC voltage to the sample solution in an exemplary gate region as shown in FIG. 2B. In method 220, detecting the presence of the first species of bacteria in the sample solution may further be performed based on sign (positive or negative) of a parameter g calculated as an indicator of the change in impedance difference peak value responsive to the change in the applied DC voltage. Referring to FIG. 2B, exemplary method 220 may further include measuring an exemplary change in impedance difference peak value responsive to an exemplary change in the applied DC voltage to the sample solution on gate region 122 (step 211) in addition to steps of exemplary method 200 illustrated in FIG. 2A.

Figure 2C:
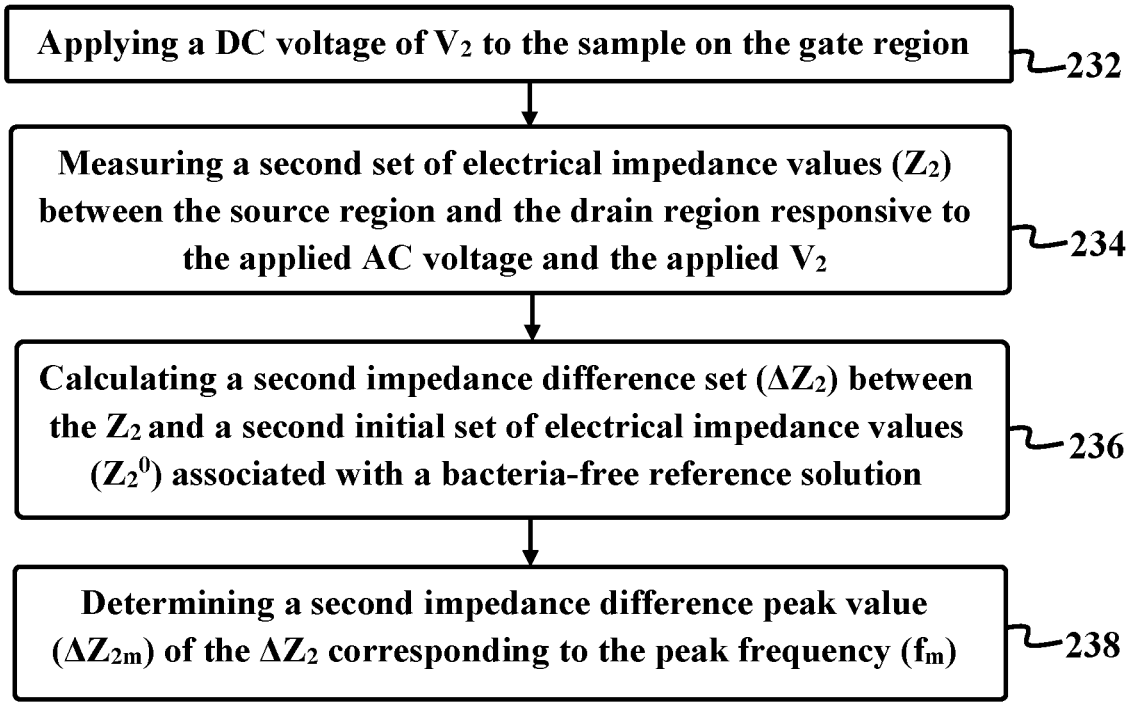
FIG. 2C shows a flowchart of an exemplary method for measuring a change in impedance difference peak value responsive to a change in an applied direct current (DC) voltage, consistent with one or more exemplary embodiments of the present disclosure.

FIG. 2C shows a flowchart of an exemplary method 230 for measuring a change in impedance difference peak value responsive to a change in the applied DC voltage (step 211), consistent with one or more exemplary embodiments of the present disclosure. In an exemplary embodiment, method 230 may include applying a second DC voltage of $V_2$ to an exemplary sample solution on gate region 122 while applying the AC voltage at the set of frequencies in the range of about 500 Hz to about 2 MHz between exemplary source electrode 118 and exemplary drain electrode 120 (step 232), measuring a second set of electrical impedance values ($Z_2$) between source region 114 and drain region 116 responsive to the applied AC voltage and the applied $V_2$ (step 234), calculating a second impedance difference set ($\Delta Z_2$) between the $Z_2$ and a second initial set of electrical impedance values ($Z_2^0$) (step 236), and determining a second impedance difference peak value ($\Delta Z_{2m}$) of the $\Delta Z_2$ respective to the peak frequency ($f_m$) (step 238).

In an exemplary embodiment, the $Z_2$ may include a second set of real part magnitude of electrical impedance respective to the set of frequencies measured while applying the AC voltage between exemplary source electrode 118 and exemplary drain electrode 120 and applying second DC voltage of $V_2$ to an exemplary sample solution on gate region 122. In an exemplary embodiment, the first DC voltage ($V_1$) and the second DC voltage ($V_2$) may include respective DC voltages in a range between 0 V and 5 V. In an exemplary embodiment, the first DC voltage ($V_1$) may include a DC voltage of about 1 V and the second DC voltage ($V_2$) may include a DC voltage of about 2 V.

In an exemplary embodiment, calculating the second impedance difference set ($\Delta Z_2$) between the $Z_2$ and the second initial set of electrical impedance values ($Z_2^0$) (step 236) may include calculating a difference between each electrical impedance value of the $Z_2$ measured at a respective frequency ($f_i$) of the set of frequencies and a respective electrical impedance value of the second initial set of electrical impedance values ($Z_2^0$) measured at the same frequency $f_i$. In an exemplary embodiment, calculating each second impedance difference may be performed using a relation defined by Equation 2:

$$(\Delta Z_2)f_i = (Z_2)f_i - (Z_2^0)f_i \quad \text{Equation 2}$$

Where, $(Z_2)f_i$ is an electrical impedance value of the $Z_2$ measured at a respective frequency ($f_i$) of the set of frequencies, $(Z_2^0)f_i$ is an electrical impedance value of the $Z_2^0$ measured at the same frequency ($f_i$), and $(\Delta Z_2)f_i$ is a value of the first impedance difference set ($\Delta Z_2$) respective to the $(Z_2)f_i$ and $(Z_2^0)f_i$.

In an exemplary embodiment, the $Z_2^0$ may include a second initial set of electrical impedance values between source region 114 and the drain region 116 of FET biosensor 102 associated with the bacteria-free reference solution while applying the AC voltage between exemplary source electrode 118 and exemplary drain electrode 120 and applying second DC voltage of $V_2$ to the bacteria-free reference solution on gate region 122. In an exemplary embodiment, exemplary method 220 may further include measuring the second initial set of electrical impedance values ($Z_2^0$). In an exemplary embodiment, measuring the $Z_2^0$ may include putting the bacteria-free reference solution on gate region 122 of FET biosensor 102 in contact with array of ZnO nanorods 124, applying the AC voltage between source electrode 118 and drain electrode 120 at the set of frequencies in a range of about 500 Hz to about 2 MHz, applying the $V_2$ utilizing DC voltage generator 106 and DC electrode 103 to the bacteria-free reference solution on gate region 122, and measuring a set of real part magnitude of electrical impedance between source region 114 and the drain region 116 versus the set of frequencies.

In an exemplary embodiment, determining the second impedance difference peak value ($\Delta Z_{2m}$) of the $\Delta Z_2$ respective to the peak frequency ($f_m$) (step 238) may include measuring a difference peak value of the $\Delta Z_2$ respective to the peak frequency ($f_m$) respective to the peak value ($\Delta Z_{1m}$) of the $\Delta Z_1$.

Referring back to FIG. 2B, step 212 of determining the bacteria indicative factors may further include determining an exemplary parameter g as an exemplary indicator of the change in impedance difference peak value responsive to the change in the applied DC voltage measured in step 211. In an exemplary embodiment, determining the parameter g may include calculating the parameter g using a relation defined by Equation 3:

$$g = \frac{\Delta Z_{2m} - \Delta Z_{1m}}{V_2 - V_1} \qquad \text{Equation 3}$$

In further detail with respect to step 214, detecting the presence of the first species of bacteria in the sample solution may include comparing exemplary determined bacteria indicative factors with a reference dataset generated for a set of reference sample solutions containing a respective set known bacteria species and detecting the presence of the first species of bacteria in the sample solution responsive to at least one of the determined bacteria indicative factors being the same as a respective factor in the reference dataset associated with the first species of bacteria. In an exemplary embodiment, detecting the presence of the first species of bacteria in the sample solution may further include determining a concentration of the first species of bacteria in the sample solution.

In an exemplary embodiment, detecting the presence of the first species of bacteria in the sample solution may include detecting the calculated $\Delta Z_{1m}$ being within a range of first reference impedance difference peak values ($\Delta Z_{1rm}$) associated with the first species of bacteria within the reference dataset. In an exemplary embodiment, detecting the presence of the first species of bacteria in the sample solution may further include detecting the determined $f_m$ being equal to a reference peak frequency ($f_{rm}$) associated with the first species of bacteria within the reference dataset. Furthermore, detecting the presence of the first species of bacteria in the sample solution may further include sign of the plurality values of the $\Delta Z_1$ being the same with sign of a plurality of at least one of first reference impedance difference sets ($\Delta Z_{1r}$) associated with the first species of bacteria within the reference dataset. Additionally, detecting the presence of the first species of bacteria in the sample solution may further include detecting the presence of the first species of bacteria in the sample solution if sign of the parameter g is the same with sign of a reference g ($g_r$) range associated with the first species of bacteria within the reference dataset.

In an exemplary embodiment, determining the $f_m$ may include detecting the $f_m$ being equal to a frequency of 1.7 MHz within the set of frequencies of the applied AC voltage. In such cases, detecting the presence of the first species of bacteria in the sample solution may include detecting a presence of helical bacteria in the sample solution if a plurality of the $\Delta Z_1$ respective to a plurality of frequencies more than 1.7 MHz have a constant value. Furthermore, detecting a presence of bacteria with longitudinal colonic growth in the sample solution if a plurality values of the $\Delta Z_1$ respective to a plurality of frequencies more than 1.7 MHz have a negative sign. Additionally, detecting a presence of at least one of spherical bacteria with non-longitudinal growth, rod-shaped bacteria with non-longitudinal growth, and combinations thereof in the sample solution if a plurality values of the $\Delta Z_1$ respective to a plurality of frequencies more than 1.7 MHz have a positive sign.

In an exemplary embodiment, detecting the presence of the first species of bacteria in the sample solution may include detecting a presence of helical bacteria in the sample solution if the determined $f_m$ is equal to a frequency of 1.7 MHz, a constant value is obtained for a plurality of the $\Delta Z_1$ respective to a plurality of frequencies more than 1.7 MHz, and the calculated g has a negative sign.

In an exemplary embodiment, exemplary method 200 (illustrated in FIG. 2A) and/or exemplary method 220 (illustrated in FIG. 2B) may further include generating an exemplary reference dataset for a plurality of solutions containing a respective plurality of known bacteria species with known concentrations of bacteria species. In an exemplary embodiment, generating the reference dataset may include generating at least one of a plurality of first reference impedance difference sets ($\Delta Z_{1r}$), a plurality of first reference impedance difference peak values ($\Delta Z_{1rm}$) ranges, a plurality of reference g ($g_r$) ranges, and a plurality of a reference peak frequencies ($f_{rm}$), and combinations thereof associated with the plurality of bacteria species.

In an exemplary embodiment, generating the reference dataset may include preparing a set of reference solutions containing a respective set of concentrations of each bacteria species of the plurality of the bacteria species and determining $\Delta Z_{1r}$, $\Delta Z_{1rm}$, $g_r$, and $f_{rm}$ for each bacteria species. In an exemplary embodiment, determining $\Delta Z_{1r}$, $\Delta Z_{1rm}$, $g_r$, and $f_{rm}$ for each bacteria species may include putting each respective reference solution on gate region 122 of FET biosensor 102 in contact with array of ZnO nanorods 124, applying the AC voltage with the set of frequencies between source electrode 118 and drain electrode 120 while applying the first DC voltage of $V_1$ to gate region 122, measuring a respective first reference set of electrical impedance values ($Z_{1r}$) between source region 114 and drain region 116 respective to the set of frequencies, calculating a respective first reference impedance difference set ($\Delta Z_{1r}$) between the $Z_{1r}$ and the first initial set $Z_1^0$, detecting a first reference peak value ($\Delta Z_{1rm}$) of the $\Delta Z_{1r}$, determining a reference peak frequency ($f_{rm}$) of the set of frequencies respective to the $\Delta Z_{1rm}$, measuring a change in reference impedance difference peak value responsive to applying the second DC voltage of $V_2$ to gate region 122 by calculating a parameter $g_r$.

In an exemplary embodiment, the first reference set of electrical impedance values ($Z_{1r}$) may include a set of real part magnitude of electrical impedance between source region 114 and drain region 116 respective to the set of frequencies.

In an exemplary embodiment, calculating the first reference impedance difference set ($\Delta Z_{1r}$) may include calculating a difference between each electrical impedance value of the $Z_{1r}$ and a respective electrical impedance value of the first initial set $Z_1^0$ using a relation defined by Equation 4:

$$(\Delta Z_{1r})f_i = (Z_{1r})f_i - (Z_1^0)f_i \qquad \text{Equation 4}$$

In an exemplary embodiment, detecting a respective first reference peak value $\Delta Z_{1rm}$ of each first reference impedance difference set $\Delta Z_{1r}$ may include determining a maximum value among values of the $\Delta Z_{1rm}$. In an exemplary embodiment, the reference peak frequency ($f_{rm}$) may be frequency of the set of frequencies respective to the determined $\Delta Z_{1rm}$.

In an exemplary embodiment, measuring the change in reference impedance difference peak value responsive to applying the $V_2$ DC voltage to gate region 122 by calculating the parameter $g_r$ is done using a relation defined by Equation 5:

$$g_r = \frac{\Delta Z_{2rm} - \Delta Z_{1rm}}{V_2 - V_1} \qquad \text{Equation 5}$$

Where, the $\Delta Z_{2rm}$ is a second reference impedance difference peak value of a second reference impedance difference set $(\Delta Z_{2r})$ at the $f_{rm}$. In an exemplary embodiment, the second reference impedance difference set $(\Delta Z_{2r})$ may be measured responsive to the applied $V_2$ while applying the AC voltage at the set of frequencies using a process similar to a process of measuring the $\Delta Z_{1r}$ responsive to the applied $V_1$ while applying the AC voltage at the set of frequencies described hereinabove.

In an exemplary embodiment, exemplary method 200 (illustrated in FIG. 2A) and/or exemplary method 220 (illustrated in FIG. 2B) may further include determining an amount of the first species of bacteria in the sample solution based on at least one of the determined $f_m$, the calculated $\Delta Z_{1m}$, and the calculated g. In an exemplary embodiment, determining the amount of the first species of bacteria in the sample solution may include determining the amount of the first species of bacteria in the sample solution equal to a $n^{th}$ concentration $(C_n)$ of the set of concentrations of the first species of bacteria associated with a first determined $f_{rm}$, a respective $n^{th}$ first reference impedance difference set $(\Delta Z_{1r})_n$, and a respective $n^{th}$ first $g_r$. In an exemplary embodiment, the amount of the first species of bacteria in the sample solution may be determined equal to the $C_n$ if the determined $f_m$ is equal to the first determined $f_{rm}$ associated with the first species of bacteria and the calculated $\Delta Z_{1m}$ is equal to a $(\Delta Z_{1rm})_n$ value associated with the $C_n$ of the set of concentrations of the first species of bacteria. In an exemplary embodiment, the amount of the first species of bacteria in the sample solution may be determined equal to the $C_n$ if the determined $f_m$ is equal to the first determined $f_{rm}$ associated with the first species of bacteria, the calculated $\Delta Z_{1m}$ is equal to a $(\Delta Z_{1rm})_n$ value associated with the $C_n$ of the set of concentrations of the first species of bacteria, and the calculated g is equal to the $n^{th}$ first $g_r$ value associated with the $C_n$ of the set of concentrations of the first species of bacteria.

Figure 4A:
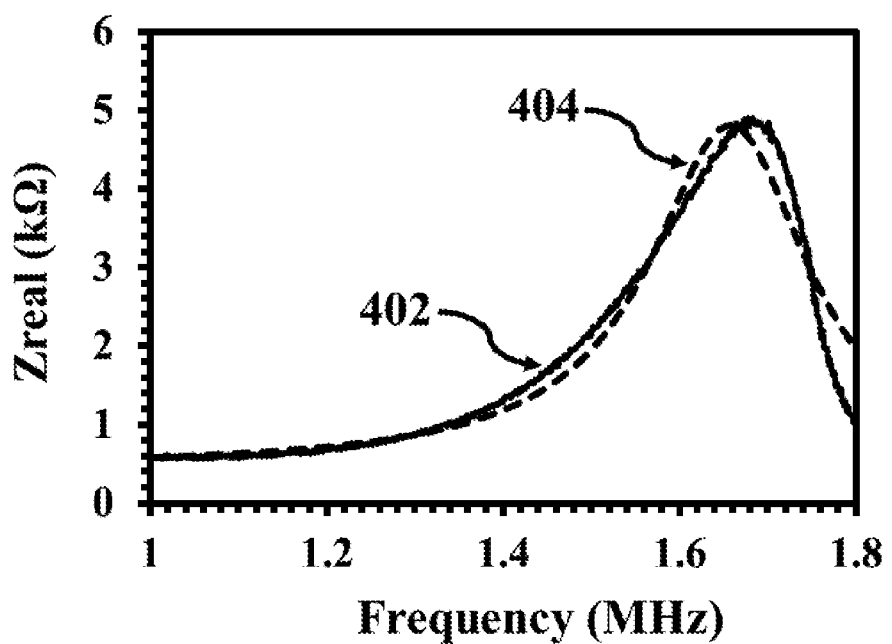
FIG. 4A shows an experimental measurement and theoretical calculation based on an equivalent circuit of source-drain impedance versus applied voltage frequency for an exemplary FET biosensor loaded by a phosphate-buffered saline (PBS) solution on gate region, consistent with one or more exemplary embodiments of the present disclosure.
Figure 4A:
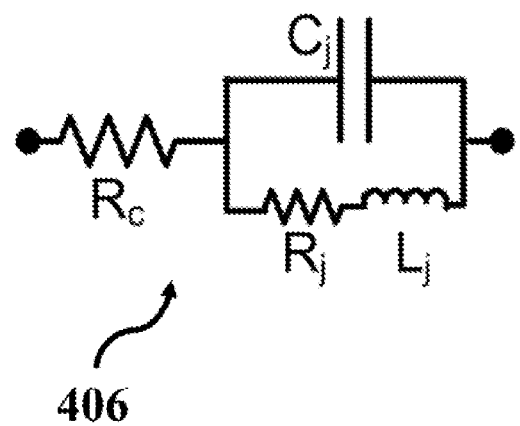

In an exemplary embodiment, source-drain impedance versus the applied AC voltage frequency for FET biosensor 102 may be simulated with an equivalent circuit 406 as shown in FIG. 4A. FIG. 4A shows an experimental measurement (solid line curve 402) and theoretical calculation (dashed line curve 404) based on an equivalent circuit 406 of source-drain impedance versus applied voltage frequency for an exemplary FET biosensor similar to FET biosensor 102 loaded by a phosphate-buffered saline (PBS) solution on gate region 122, consistent with one or more exemplary embodiments of the present disclosure. Theoretical calculations may be done based on exemplary equivalent circuit 406 for an exemplary FET biosensor similar to FET biosensor 102; thereby, exemplary curve 404 may be fitted to experimentally measured data of curve 402. In an exemplary embedment, circuit parameters in the presence of bacteria-free PBS solution may be calculated as $R_c$=31.9 mΩ, $R_j$=10.47Ω, $C_j$=0.117 μF and $L_j$=5.2×10-8 H. Rc may be an exemplary channel resistance, and Cj and Lj may be junction capacitance and inductance, respectively. Moreover, Rj may be junction charge transfer resistance. Loading different bacteria on gate region 122 of FET biosensor 102 may lead to change an exemplary channel resistance and may affect exemplary junction parameters.

Figure 4B:
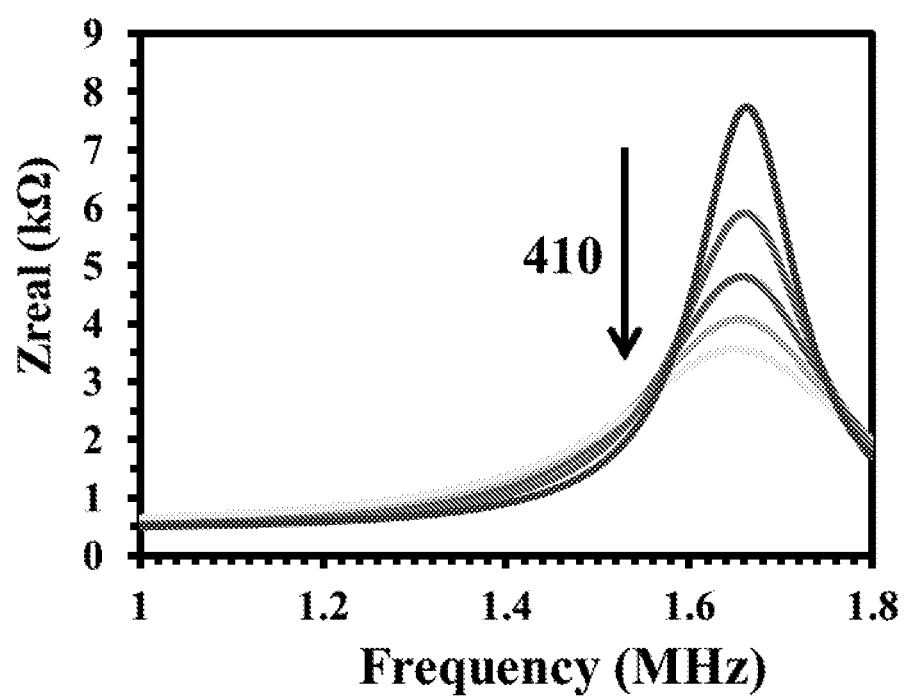
FIG. 4B shows an exemplary set of theoretically calculated source-drain impedance curves with different $R_c$ values, consistent with one or more exemplary embodiments of the present disclosure.
Figure 4C:
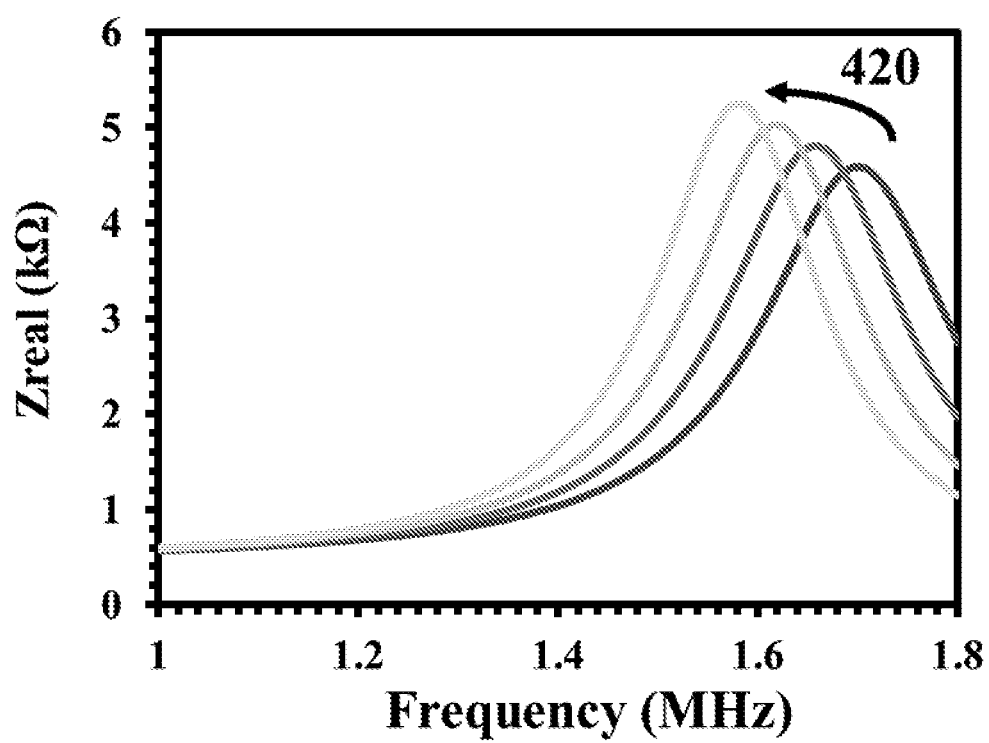
FIG. 4C shows an exemplary set of theoretically calculated source-drain impedance curves with different $L_j$ values, consistent with one or more exemplary embodiments of the present disclosure.
Figure 4D:
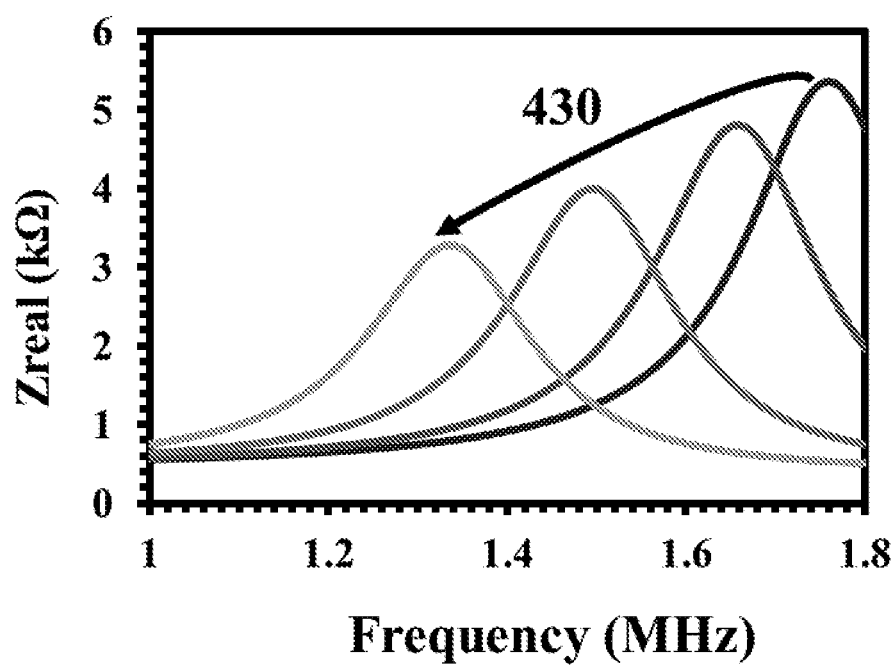
FIG. 4D shows an exemplary set of theoretically calculated source-drain impedance curves with different $C_j$ values, consistent with one or more exemplary embodiments of the present disclosure.

FIG. 4B shows an exemplary set of theoretically calculated source-drain impedance curves with different $R_c$ values, consistent with one or more exemplary embodiments of the present disclosure. Exemplary arrow 410 shows a direction of curves shift by increasing $R_c$. Furthermore, FIG. 4C shows an exemplary set of theoretically calculated source-drain impedance curves with different $L_j$ values, consistent with one or more exemplary embodiments of the present disclosure. Exemplary arrow 420 shows a direction of curves shift by increasing $L_j$. Moreover, FIG. 4D shows an exemplary set of theoretically calculated source-drain impedance curves with different $C_j$ values, consistent with one or more exemplary embodiments of the present disclosure. Exemplary arrow 430 shows a direction of curves shift by increasing $C_j$. As shown in these figures, decreasing channel resistance $(R_c)$ may lead to an increment in the impedance peak. In an exemplary embodiment, different electrostatic behavior of bacteria species may be monitored and distinctive by monitoring $R_c$. In an exemplary embodiment, increasing cell concentration of *Escherichia coli* (*E. coli*) and *Spirulina platensis* (*S. platensis*) may decrease the Rc, while increasing cell concentration of *Acetobacter aceti* (*A. aceti*) and *Nostoc ellipsosporum* (*N. ellipsosporum*) may increase Rc. In an exemplary embodiment, changing Lj and Cj not only may change a peak intensity, but also may lead to a peak shift in impedance spectra of FET biosensor 102. Therefore, loading different bacteria species on gate region 122 may affects Lj and Cj leading to different impedance spectra.

In an exemplary embodiment, exemplary method 200 (illustrated in FIG. 2A) and/or exemplary method 220 (illustrated in FIG. 2B) may further include differentiating a presence of gram-positive bacteria and gram-negative bacteria in an exemplary sample solution. In an exemplary embodiment, differentiating the presence of gram-positive bacteria and gram-negative bacteria in an exemplary sample solution may include exposing an exemplary sample solution placed on gate region 122 to blue light irradiation, applying the AC voltage with the set of frequencies of 500 Hz to 2 MHz between source electrode 118 and drain electrode 120, applying the first DC voltage of $V_1$ to an exemplary sample solution on gate region 122, measuring a third set of electrical impedance values $(Z_3)$ between source region 114 and drain region 116 responsive to the applied AC voltage and the applied $V_1$ in the presence of blue light radiation, calculating a third impedance difference set $(\Delta Z_3)$, detecting a third impedance difference peak value $(\Delta Z_{3m})$ of the $\Delta Z_3$ respective to the peak frequency $(f_m)$, and differentiating the presence of gram-positive bacteria and gram-negative bacteria in an exemplary sample solution.

In an exemplary embodiment, the $Z_3$ may include a third set of real part magnitude of electrical impedance respective to the set of frequencies.

In an exemplary embodiment, calculating the $\Delta Z_3$ may include calculating a difference between each electrical impedance value of the $Z_3$ measured at a respective frequency $(f_i)$ of the set of frequencies and a respective electrical impedance value of the initial set of electrical impedance values $(Z_1^0)$ measured at the same frequency $f_i$. In an exemplary embodiment, calculating each third impedance difference may be done using a relation defined by following Equation 6:

$$(\Delta Z_3)f_i = (Z_3)f_i - (Z_1^0)f_i \qquad \text{Equation 6}$$

In an exemplary embodiment, differentiating the presence of gram-positive bacteria and gram-negative bacteria in an exemplary sample solution may include detecting a presence of gram-negative bacteria in exemplary sample solution if the calculated $\Delta Z_{1m}$ and $\Delta Z_{3m}$ have the same sign. In another exemplary embodiment, differentiating the presence of gram-positive bacteria and gram-negative bacteria in exemplary sample solution may include detecting a presence of gram-positive bacteria in exemplary sample solution if the calculated $\Delta Z_{1m}$ and $\Delta Z_{3m}$ have opposite signs.

Figure 3:
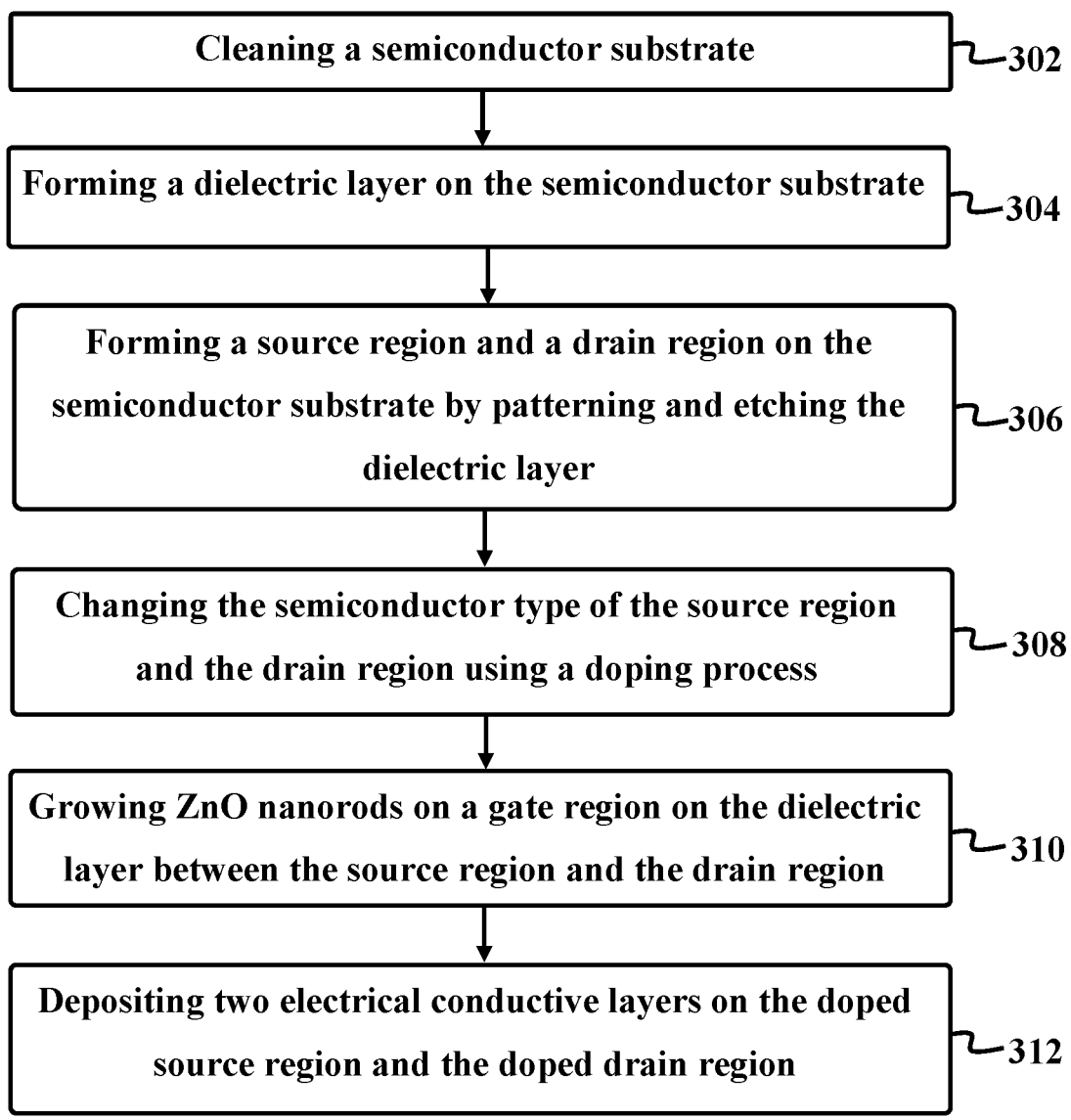
FIG. 3 shows an exemplary method for fabricating an exemplary FET biosensor, consistent with one or more exemplary embodiments of the present disclosure.

In an exemplary embodiment, exemplary method 200 (illustrated in FIG. 2A) and/or exemplary method 220 (illustrated in FIG. 2B) may further include fabricating exemplary FET biosensor 102. In an exemplary embodiment, fabricating an exemplary FET biosensor 10 may occur before step 202 in both method 200 and method 220. FIG. 3 shows exemplary method 300 for fabricating exemplary FET biosensor 102, consistent with one or more exemplary embodiments of the present disclosure. Exemplary method 300 may include removing impurities from exemplary semiconductor substrate 110 by cleaning semiconductor substrate 110 (step 302), forming dielectric layer 112 on semiconductor substrate 110 (step 304), forming source region 114 and drain region 116 on semiconductor substrate 110 by removing dielectric layer 112 in source region 114 and drain region 116 (step 306), increasing electrical conductivity of source region 114 and drain region 116 using a doping process (step 308), growing array of ZnO nanorods 124 on gate region 122 of dielectric layer 112 between source region 114 and drain region 116 (step 310), and forming source electrode 118 and drain electrode 120 by depositing a first electrical conductive layer on source region 114 and a second electrical conductive layer on drain region 116 (step 312).

In an exemplary embodiment, step 302 may include removing impurities from exemplary semiconductor substrate 110 by cleaning semiconductor substrate 110. In an exemplary embodiment, cleaning semiconductor substrate 110 may include cleaning a silicon (Si) wafer using a RCA #1 (Radio Corporation of America) solution.

Furthermore, step 304 may include forming dielectric layer 112 on semiconductor substrate 110. In an exemplary embodiment, forming dielectric layer 112 may include growing a layer of silicon dioxide (SiO$_2$) over a top surface of semiconductor substrate 110. In an exemplary embodiment, forming dielectric layer 112 may include thermal growth of a 100 nm thick SiO$_2$ layer at 1100° C. on an exemplary cleaned Si.

Moreover, step 306 may include forming source region 114 and drain region 116 on semiconductor substrate 110 by removing dielectric layer 112 in source region 114 and drain region 116. In an exemplary embodiment, forming source region 114 and drain region 116 may include patterning a layout of source region 114 and drain region 116 on dielectric layer 112 using a standard photolithography process and etching dielectric layer 112 within the patterned layout; thereby, resulting in removing dielectric layer 112 in source region 114 and drain region 116.

Additionally, step 308 may include increasing electrical conductivity of source region 114 and drain region 116 using a doping process. In an exemplary embodiment, increasing electrical conductivity of source region 114 and drain region 116 may include changing semiconductor characteristics of source region 114 and drain region 116 by doping source region 114 and drain region 116. In an exemplary embodiment, increasing electrical conductivity of source region 114 and drain region 116 may include doping source region 114 and drain region 116 with a dopant agent including at least one of phosphorus (P), arsenic (As), antimony (Sb), Bismuth (Bi), lithium (Li), Gallium (Ga), Aluminum (Al), boron (B), and indium (In). In an exemplary embodiment, an exemplary dopant agent for an exemplary doping process may be selected based on a type of semiconductor substrate 110. In an exemplary embodiment, at least one of Gallium (Ga), Aluminum (Al), boron (B), and indium (In) may be used for doping a p-type semiconductor substrate 110. In an exemplary embodiment, at least one of phosphorus (P), arsenic (As), antimony (Sb), Bismuth (Bi), and lithium (Li) may be used for doping a n-type semiconductor substrate 110.

Moving to step 310, array of ZnO nanorods 124 may be grown on gate region 122 of dielectric layer 112 between source region 114 and drain region 116. In an exemplary embodiment, ZnO nanorods 124 may be grown on top surface of gate region 122 using a hydrothermal process.

In an exemplary embodiment, step 312 may include forming source electrode 118 and drain electrode 120 by depositing an exemplary first electrical conductive layer on source region 114 and an exemplary second electrical conductive layer on drain region 116. In an exemplary embodiment, forming source electrode 118 and drain electrode 120 may include adhering or depositing two respective metal layers on source region 114 and drain region 116. In an exemplary embodiment, source electrode 118 and drain electrode 120 may include two respective layers of gold (Au).

Furthermore, an exemplary method 300 of fabrication of exemplary FET biosensor 102 may include enclosing exemplary gate region 122 with grown array of ZnO nanorods 124 thereon by exemplary container 126. In an exemplary embodiment, container 126 may include a container with an open top side and an open bottom side. In an exemplary embodiment, container 126 may be made of glass.

Figure 5:
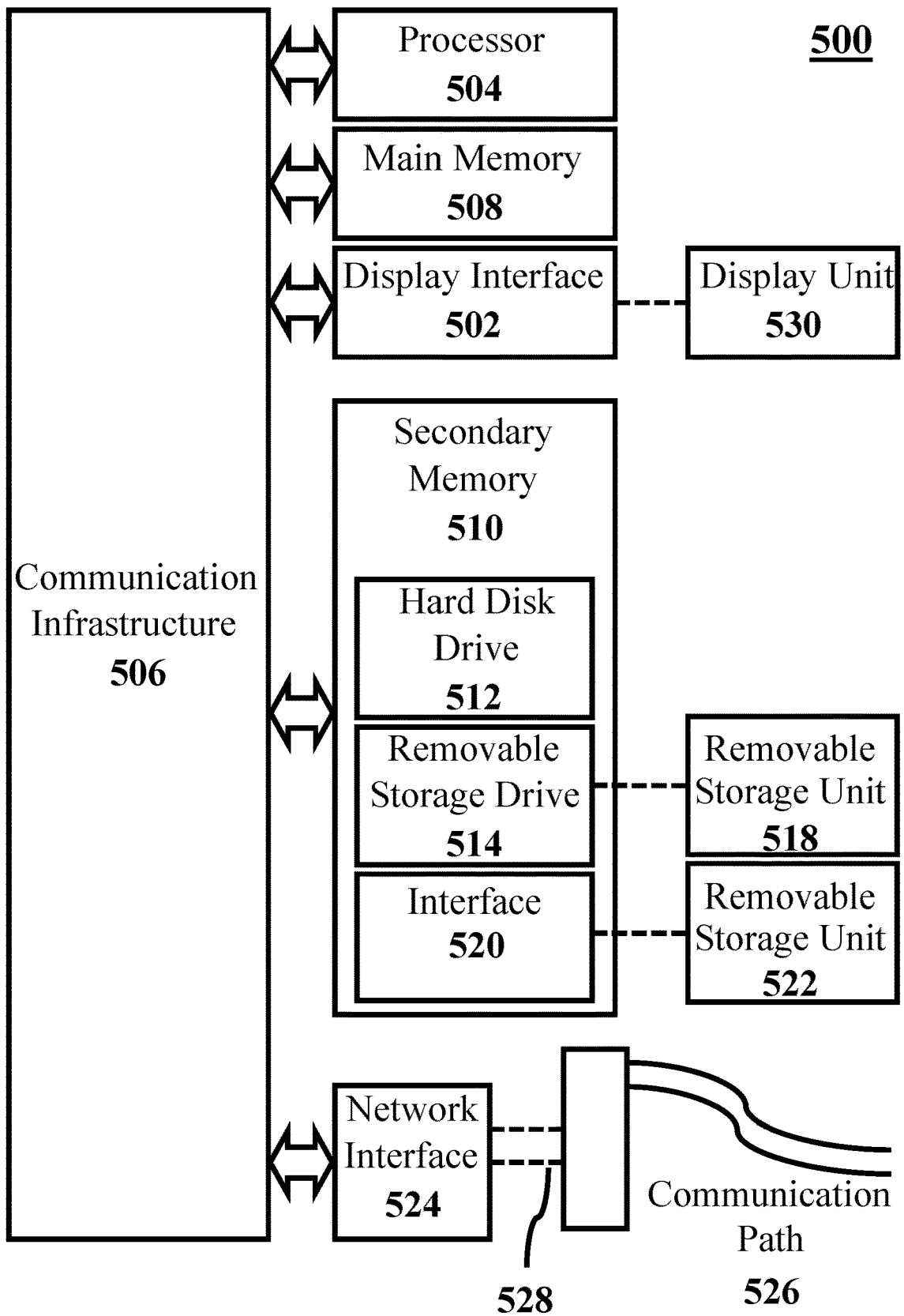
FIG. 5 shows an example computer system in which an embodiment of the present disclosure, or portions thereof, may be implemented as computer-readable code, consistent with one or more exemplary embodiments of the present disclosure.

In an exemplary embodiment, one or more steps of methods 200, 220, and 230 may be performed by processing unit 108. FIG. 5 shows an example computer system 500 in which an embodiment of the present disclosure, or portions thereof, may be implemented as computer-readable code, consistent with one or more exemplary embodiments of the present disclosure. For example, computer system 500 may include an example of processing unit 108 illustrated in FIG. 1, and one or more steps of exemplary methods 200, 220, and 230 presented in FIGS. 2A-2C, may be implemented in computer system 500 using hardware, software, firmware, tangible computer readable media having instructions stored thereon, or a combination thereof and may be implemented in one or more computer systems or other processing systems. Hardware, software, or any combination of such may embody any of the modules and components in FIG. 1.

If programmable logic is used, such logic may execute on a commercially available processing platform or a special purpose device. One ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the present disclosure is described in terms of this example computer system 500. After reading this description, it will become apparent to a person skilled in the relevant art how to implement the invention using other computer systems and/or computer architectures.

Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 504 may be a special purpose or a general-purpose processor device. As will be appreciated by persons skilled in the relevant art, processor device 504 may also be a single processor in a multi-core/multiprocessor system, such system operating alone, or in a cluster of computing devices operating in a cluster or server farm. Processor device 504 may be connected to a communication infrastructure 506, for example, a bus, message queue, network, or multi-core message-passing scheme.

In an exemplary embodiment, computer system 500 may include a display interface 502, for example a video connector, to transfer data to a display unit 530, for example, a monitor. Computer system 500 may also include a main memory 508, for example, random access memory (RAM), and may also include a secondary memory 510. Secondary memory 510 may include, for example, a hard disk drive 512, and a removable storage drive 514. Removable storage drive 514 may include a floppy disk drive, a magnetic tape drive, an optical disk drive, a flash memory, or the like. Removable storage drive 514 may read from and/or write to a removable storage unit 518 in a well-known manner. Removable storage unit 518 may include a floppy disk, a magnetic tape, an optical disk, etc., which may be read by and written to by removable storage drive 514. As will be appreciated by persons skilled in the relevant art, removable storage unit 518 may include a computer usable storage medium having stored therein computer software and/or data.

In alternative embodiments, secondary memory 510 may include other similar means for allowing computer programs or other instructions to be loaded into computer system 500. Such means may include, for example, a removable storage unit 522 and an interface 520. Examples of such means may include a program cartridge and cartridge interface (such as that found in video game devices), a removable memory chip (such as an EPROM, or PROM) and associated socket, and other removable storage units 522 and interfaces 520 which allow software and data to be transferred from removable storage unit 522 to computer system 500.

Computer system 500 may also include a communications interface 524. Communications interface 524 allows software and data to be transferred between computer system 500 and external devices. Communications interface 524 may include a modem, a network interface (such as an Ethernet card), a communications port, a PCMCIA slot and card, or the like. Software and data transferred via communications interface 524 may be in the form of signals, which may be electronic, electromagnetic, optical, or other signals capable of being received by communications interface 524. These signals may be provided to communications interface 524 via a communications path 526. Communications path 526 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 518, removable storage unit 522, and a hard disk installed in hard disk drive 512. Computer program medium and computer usable medium may also refer to memories, such as main memory 508 and secondary memory 510, which may be memory semiconductors (e.g. DRAMs, etc.).

Computer programs (also called computer control logic) are stored in main memory 508 and/or secondary memory 510. Computer programs may also be received via communications interface 524. Such computer programs, when executed, enable computer system 500 to implement different embodiments of the present disclosure as discussed herein. In particular, the computer programs, when executed, enable processor device 504 to implement the processes of the present disclosure, such as the operations in exemplary methods 200, 220, and 230 illustrated by FIGS. 2A-2C, discussed above. Accordingly, such computer programs represent controllers of computer system 500. Where an exemplary embodiment of method 100 is implemented using software, the software may be stored in a computer program product and loaded into computer system 500 using removable storage drive 514, interface 520, and hard disk drive 512, or communications interface 524.

Embodiments of the present disclosure also may be directed to computer program products including software stored on any computer useable medium. Such software, when executed in one or more data processing device, causes a data processing device to operate as described herein. An embodiment of the present disclosure may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nano-technological storage device, etc.).

EXAMPLE 1

Fabrication of a FET Biosensor

Figure 6:
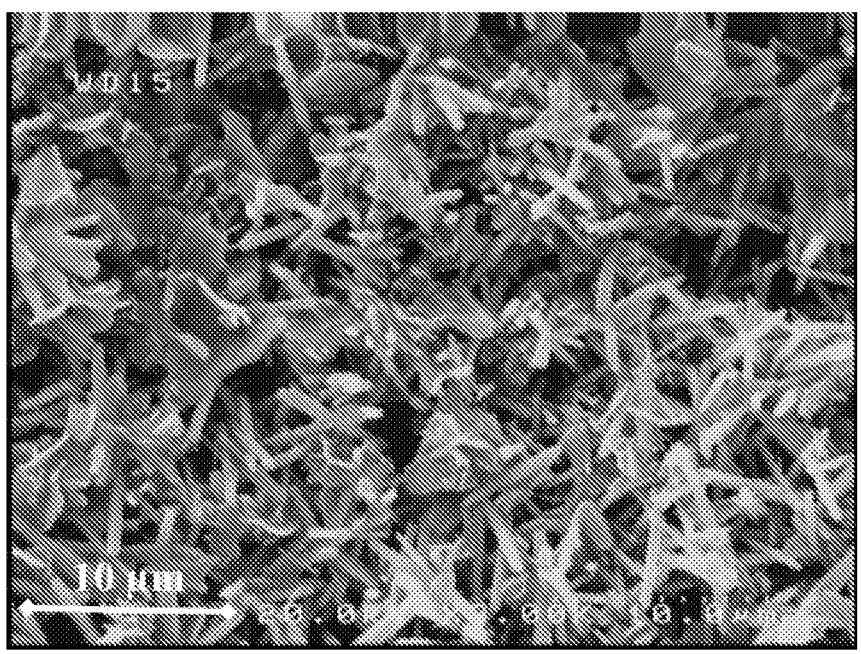
FIG. 6 shows field emission scanning electron microscopy (FESEM) images of ZnO nanorods grown on an exemplary gate region of an exemplary fabricated FET biosensor with two magnifications, consistent with one or more exemplary embodiments of the present disclosure.
Figure 6:
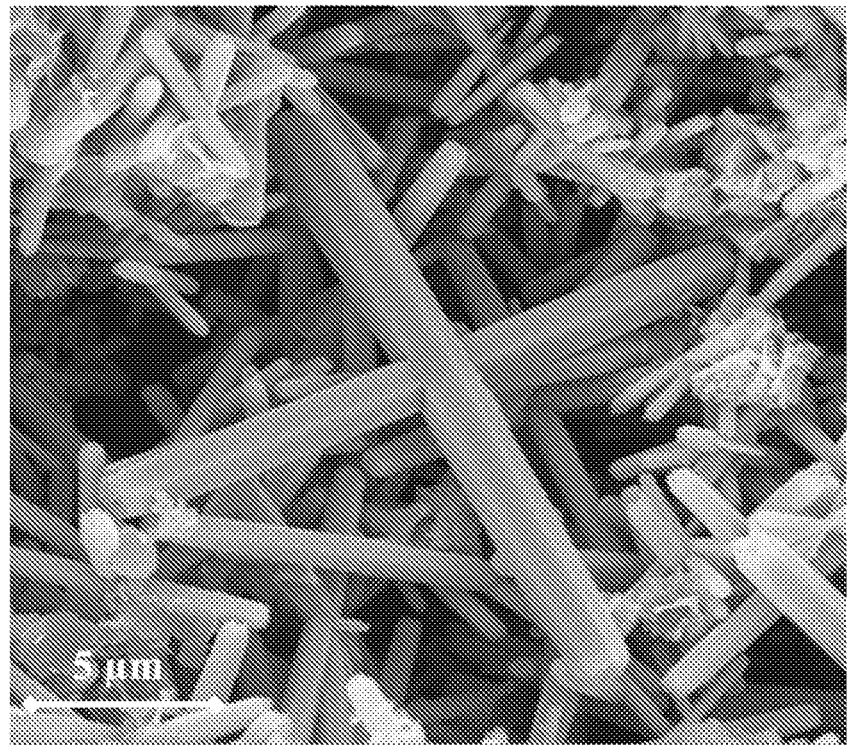

In this example, an exemplary FET biosensor similar to FET biosensor 102 was fabricated via an exemplary method similar to exemplary method 300 described hereinabove. A p-type (100) silicon (Si) wafer was cleaned. For cleaning the silicon wafer, it was placed in deionized (DI) water and heated up to 70° C. $H_2O_2$ and $NH_3$ (DI water:$H_2O_2$:$NH_3$=5:1:1 volume fraction) were then added and the solution was kept at 70° C. for 10 min. Then, the silicon wafer was rinsed with DI water to remove contaminants. Fabrication process was then followed by thermal growth of a 100 nm thick $SiO_2$ layer at 1100° C. on cleaned Si wafer to form a dielectric layer between the Si wafer and an exemplary top gate region. After that, standard photolithography following by an etching process was performed on $SiO_2$ to achieve a desired pattern for source and drain areas. In order to n-type doping of the Si wafer, the prepared Si wafer with the dielectric layer was then placed in a quartz tube furnace at 750° C., and oxygen gas and argon gas were flown simultaneously into the tube for 30 min to bubble $POCl_3$ liquid. On the gate region of an exemplary biosensor, ZnO nanorods were deposited by hydrothermal method. ZnO nanorods were synthesized by putting samples into an equimolar (7 mM) aqueous solution of Zinc Nitrate ($Zn(NO_3)_2$) and hexamethylenetetramine (HMTA; C6H12N4). The fabricated biosensor was submerged in the solution and was kept in oven at temperature 90° C. for 24 hours. After 24 hours, samples the fabricated biosensor was dipped in DI water and blow dried with nitrogen. After that, the fabricated biosensor was annealed at 450° C. for one hour. An annealing process may enhance ZnO adhesion to $SiO_2$ layer in presence of an exemplary bacteria-containing solution. FIG. 6 shows field emission scanning electron microscopy (FESEM) images 602 and 604 of ZnO nanorods grown on an exemplary gate region of an exemplary fabricated FET biosensor with two magnifications, consistent with one or more exemplary embodiments of the present disclosure. Furthermore, two metal layers were deposited on the respective source and drain regions by shadow masking process to form source and drain electrodes. Then, a plexiglass container was placed and fixed around the gate region of the fabricated biosensor for bacteria loading and preventing penetration of biomaterials into the source and drain electrodes. Finally, an Ag/AgCl electrode was put inside the container for applying a solution gate DC voltage to an exemplary sample solution placed inside the container on the gate region.

EXAMPLE 2

Impedance Measurements of the FET Biosensor for Detecting Bacteria in a Sample Solution In this example, several bacteria with different species and shapes were used for investigating impedimetric sensor characteristics. At the first step of measurements, exemplary fabricated FET biosensors according to EXAMPLE 1 hereinabove were exposed to different bacterial strains including *Escherichia coli* (*E. coli*), *Acetobacter aceti* (*A. aceti*), *Spirulina platensis* (*S. platensis*), and *Nostoc ellipsosporum* (*N. ellipsosporum*). Bacteria-containing solutions were prepared by cultivating *Escherichia coli* (PTCC 1276), *Acetobacter aceti* (PTCC 1051), and *Nostoc ellipsosporum* (PTCC 1659) in Luria-Bertani broth (LB), mannitol salt broth, and BG-11 liquid medium, respectively. A Cyanobacteria, *Spirulina platensis*, was also provided and grown in standard Zarrouk's medium. After fabricated FET biosensors being soaked in bacterial suspensions, FESEM analysis was done to confirm an effective adhesion of bacteria to exemplary ZnO nanorods covered on an exemplary gate region of fabricated FET biosensors. An exemplary method similar to methods 200 and 220 was performed for impedance measurements.

Figure 7:
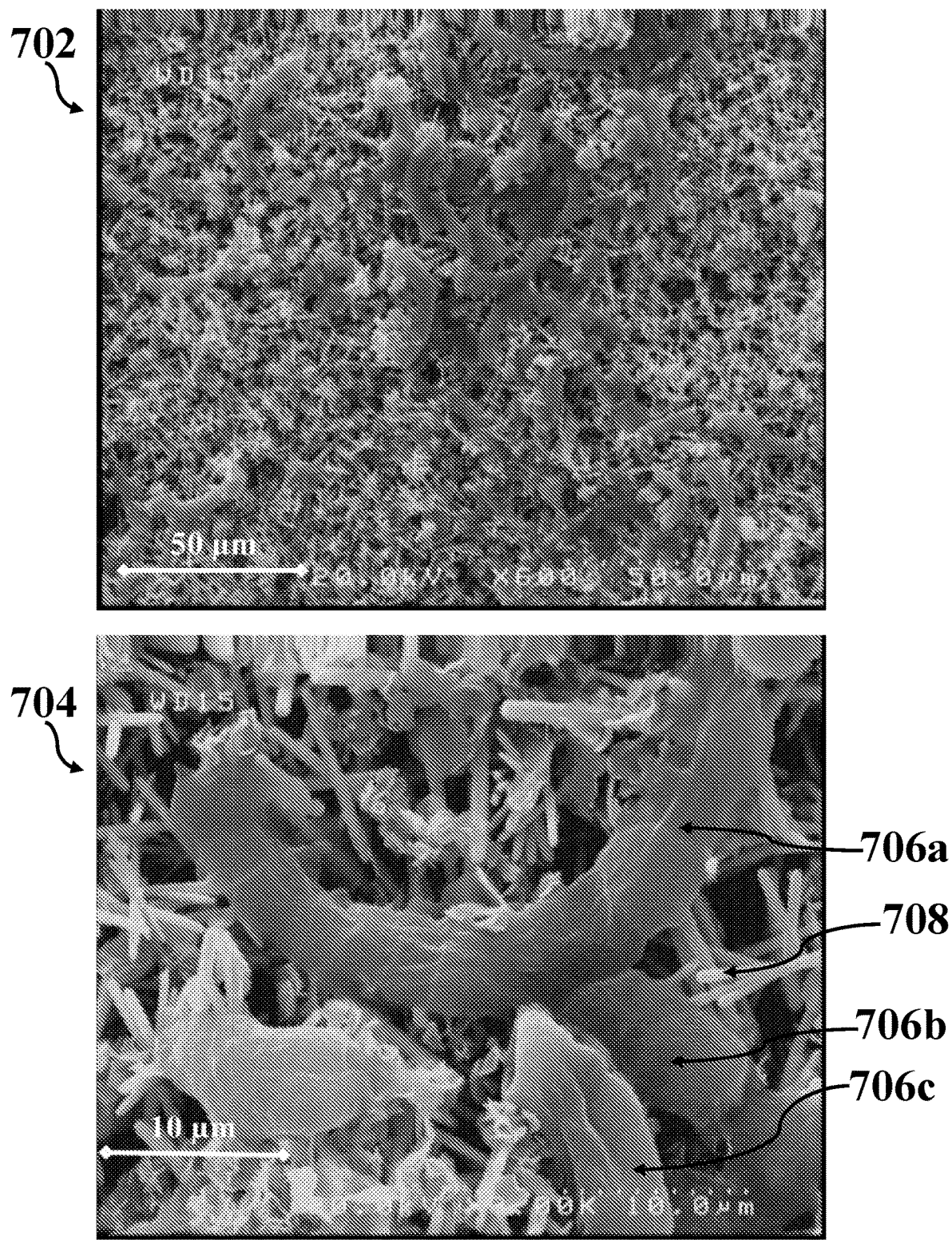
FIG. 7 shows FESEM images with two magnifications of exemplary Spirulina platensis (S. platensis) bacteria adhered to ZnO nanorods on an exemplary gate region of an exemplary fabricated FET biosensor, consistent with one or more exemplary embodiments of the present disclosure.

FIG. 7 shows FESEM images 702 and 704 with two magnifications of exemplary *Spirulina platensis* (*S. platensis*) bacteria 706*a*, 706*b*, and 706*c* adhered to ZnO nanorods 708 on an exemplary gate region of an exemplary fabricated FET biosensor, consistent with one or more exemplary embodiments of the present disclosure. Exemplary images 702 and 704 may reveal proper adhesion of bacteria 706*a*, 706*b*, and 706*c* on exemplary nanorods 708. Exemplary ZnO nanorods may be covered with a positively charged electrical double layer in a solution with bacteria cells. Hence, bacteria cells with negatively charged surfaces may attach to ZnO nanorods.

Figure 8A:
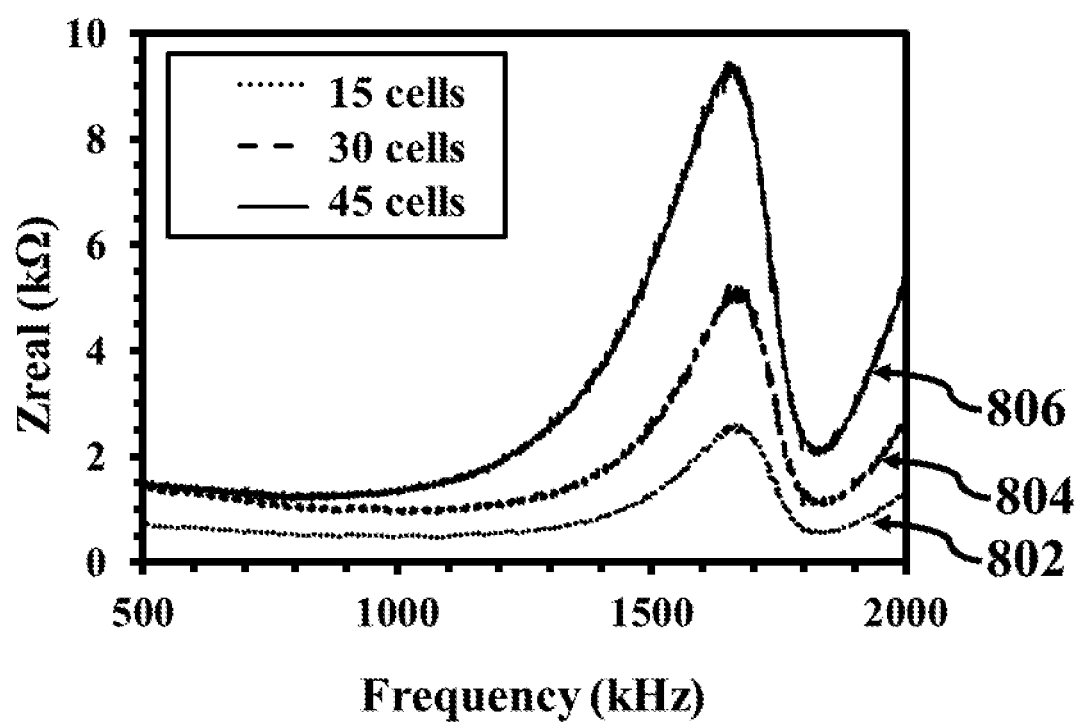
FIG. 8A shows real part of source-drain impedance versus frequency of an applied source-drain AC voltage while placing a solution containing Escherichia coli (E. coli) bacteria with different bacteria concentrations, including 15 cells, 30 cells, and 45 cells on gate region of an exemplary fabricated FET biosensor, consistent with one or more exemplary embodiments of the present disclosure.
Figure 8B:
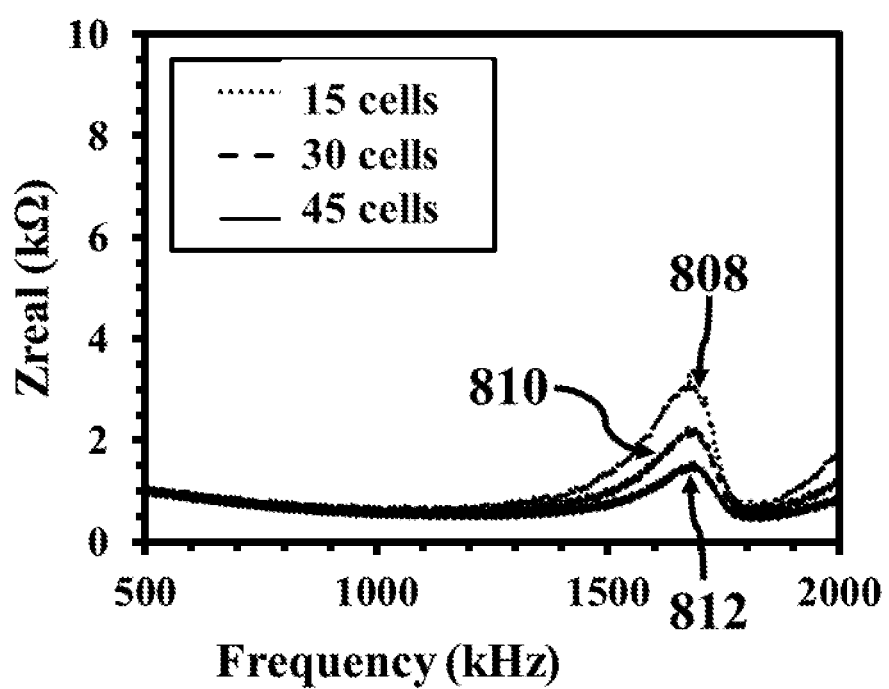
FIG. 8B shows real part of source-drain impedance versus frequency of an applied source-drain AC voltage while placing a solution containing Acetobacter aceti (A. aceti) bacteria with different bacteria concentrations, including 15 cells, 30 cells, and 45 cells on gate region of an exemplary fabricated FET biosensor, consistent with one or more exemplary embodiments of the present disclosure.
Figure 8C:
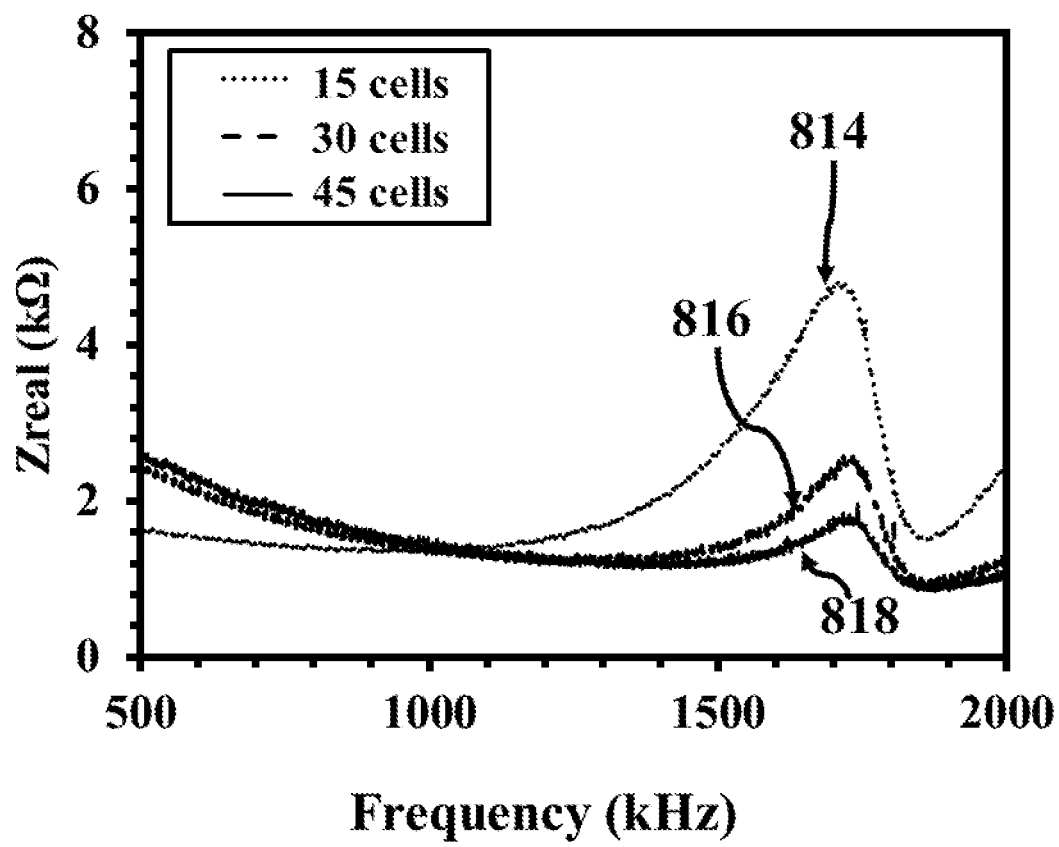
FIG. 8C shows real part of source-drain impedance versus frequency of an applied source-drain AC voltage while placing a solution containing Nostoc ellipsosporum (N. ellipsosporum) bacteria with different bacteria concentrations, including 15 cells, 30 cells, and 45 cells on gate region of an exemplary fabricated FET biosensor, consistent with one or more exemplary embodiments of the present disclosure.
Figure 8D:
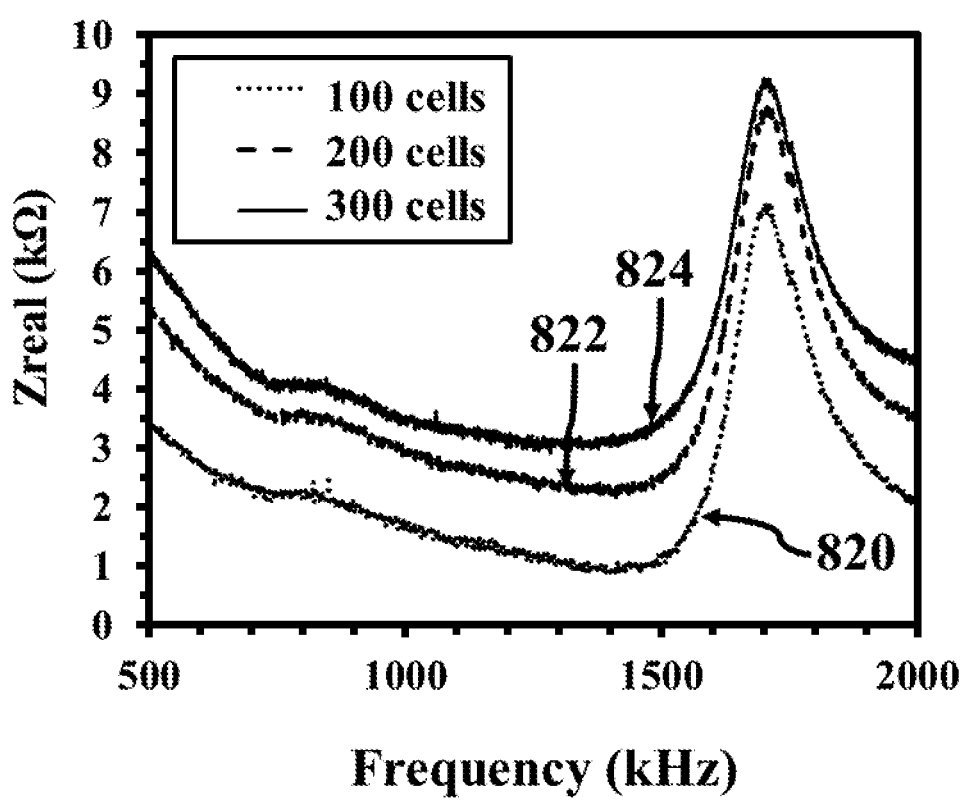
FIG. 8D shows real part of source-drain impedance versus frequency of an applied source-drain AC voltage while placing a solution containing Spirulina platensis (S. platensis) bacteria with different bacteria concentrations, including 100 cells, 200 cells, and 300 cells on gate region of an exemplary fabricated FET biosensor, consistent with one or more exemplary embodiments of the present disclosure.

For sensitivity measurements and analysis of exemplary fabricated FET biosensors, real part of source-drain impedance versus a frequency of an applied AC source-drain voltage for different bacteria loading was measured and plotted. FIG. 8A shows real part of source-drain impedance versus frequency of an applied source-drain AC voltage while placing a solution containing *Escherichia coli* (*E. coli*) bacteria with different bacteria concentrations, including 15 cells (curve 802), 30 cells (curve 804), and 45 cells (curve 806) on gate region of an exemplary fabricated FET biosensor, consistent with one or more exemplary embodiments of the present disclosure. Similar figures were plotted for loading *A. aceti*, *S. platensis*, and *N. ellipsosporum* on exemplary gate region. FIG. 8B shows real part of source-drain impedance versus frequency of an applied source-drain AC voltage while placing a solution containing *Acetobacter aceti* (*A. aceti*) bacteria with different bacteria concentrations, including 15 cells (curve 808), 30 cells (curve 810), and 45 cells (curve 812) on gate region of an exemplary fabricated FET biosensor, consistent with one or more exemplary embodiments of the present disclosure. FIG. 8C shows real part of source-drain impedance versus frequency of an applied source-drain AC voltage while placing a solution containing *Nostoc ellipsosporum* (*N. ellipsosporum*) bacteria with different bacteria concentrations, including 15 cells (curve 814), 30 cells (curve 816), and 45 cells (curve 818) on gate region of an exemplary fabricated FET biosensor, consistent with one or more exemplary embodiments of the present disclosure. FIG. 8D shows real part of source-drain impedance versus frequency of an applied source-drain AC voltage while placing a solution containing *Spirulina platensis* (*S. platensis*) bacteria with different bacteria concentrations, including 100 cells (curve 820), 200 cells (curve 822), and 300 cells (curve 824) on gate region of an exemplary fabricated FET biosensor, consistent with one or more exemplary embodiments of the present disclosure. As shown in FIGS. 8A-8D, source-drain impedance may be sensitive to number of cells. Impedance and an exemplary impedance peak increase by increasing number of *E. coli* and *S. platensis* cells, but impedance values and an exemplary impedance peak decrease by increasing number of *A. aceti* and *N. ellipsosporum* cells. Shapes of curves are also different for exemplary FET biosensors loaded by different bacteria species.

Figure 8E:
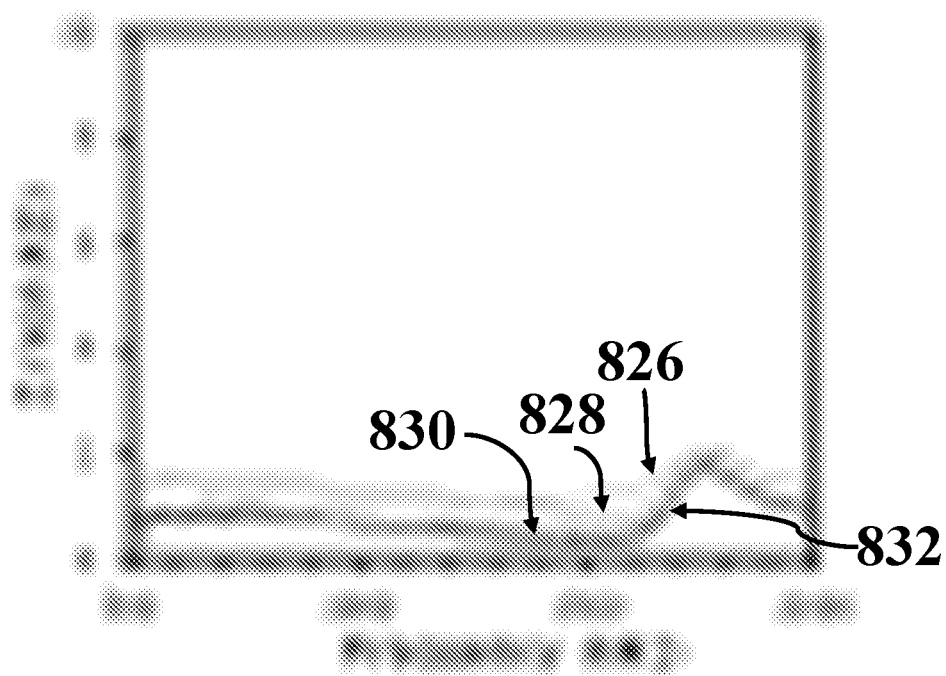
FIG. 8E shows real part of source-drain impedance versus frequency of an applied source-drain AC voltage while placing solutions containing E. coli, S. platensis, N. ellipsosporum, and A. aceti on gate region of an exemplary fabricated FET biosensor without ZnO nanorods, consistent with one or more exemplary embodiments of the present disclosure.

FIG. 8E shows real part of source-drain impedance versus frequency of an applied source-drain AC voltage while placing solutions containing *E. coli* (curve 826), *S. platensis* (curve 828), *N. ellipsosporum* (curve 830), and *A. aceti* (curve 832) on gate region of an exemplary fabricated FET biosensor without ZnO nanorods, consistent with one or more exemplary embodiments of the present disclosure. Comparing with the ZnO coated FET biosensors (FIGS. 8A-8D), an impedance change is very low; meaning that there are not enough bacteria cells on gate surface to change the impedance. As a result, ZnO nanorods facilitate bacteria capturing on gate surface and improve a sensitivity of an exemplary FET biosensor. The overall shape of an exemplary FET impedance spectrum may be due to FET biosensor impedance and the differences are due to bacteria loading.

Figure 9A:
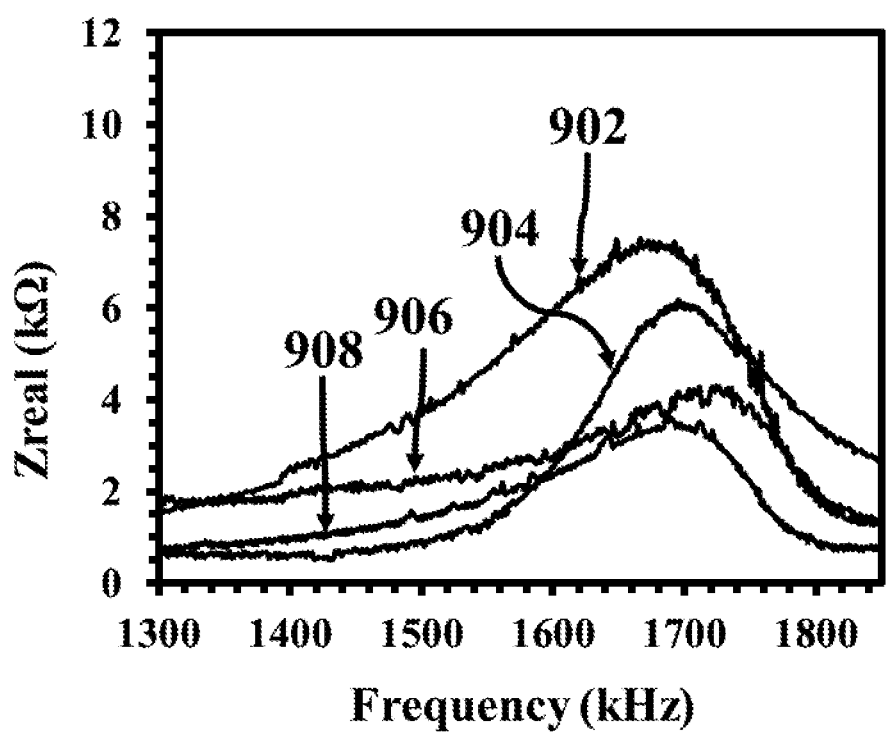
FIG. 9A shows real part of source-drain impedance versus frequency of an applied source-drain AC voltage while placing solutions containing E. coli, S. platensis, N. ellipsosporum, and A. aceti on gate region of an exemplary fabricated FET biosensor, consistent with one or more exemplary embodiments of the present disclosure.
Figure 9B:
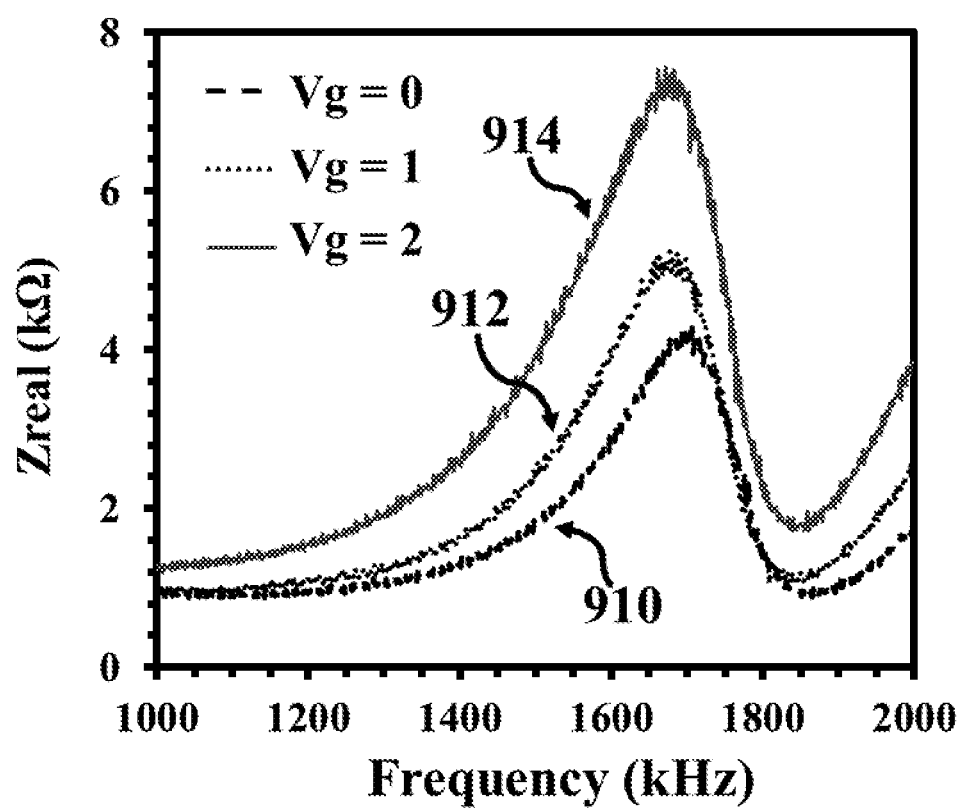
FIG. 9B shows real part of source-drain impedance versus frequency of an applied source-drain AC voltage in the presence of a solution containing E. coli on gate region of an exemplary fabricated FET biosensor for different DC gate voltages of 0 V, 1 V, and 2 V, consistent with one or more exemplary embodiments of the present disclosure.
Figure 9C:
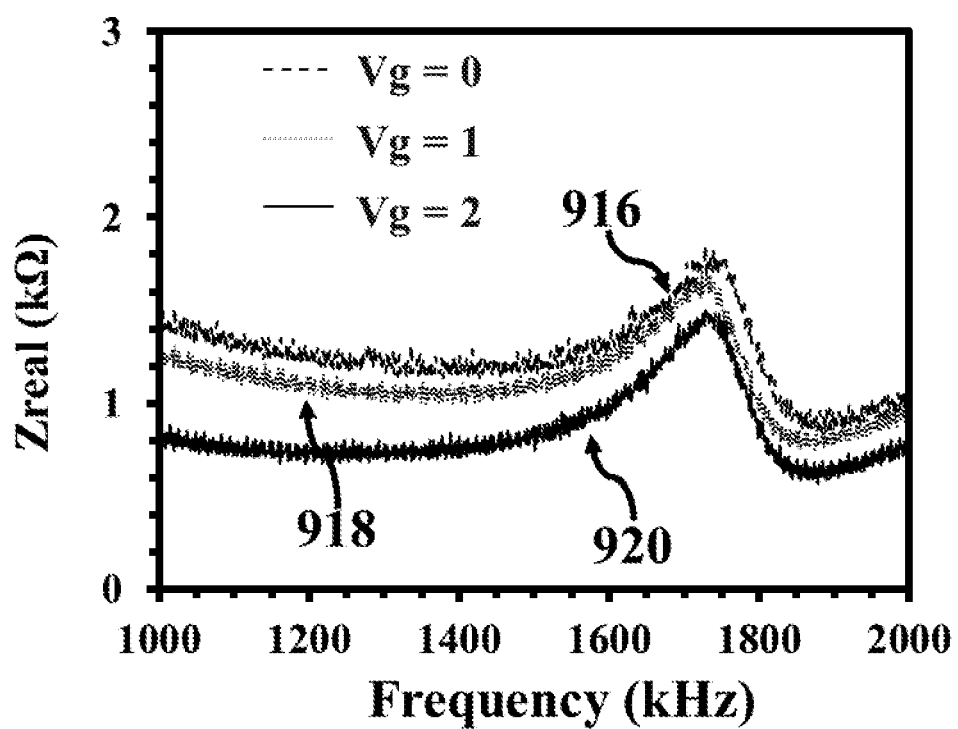
FIG. 9C shows real part of source-drain impedance versus frequency of an applied source-drain AC voltage in the presence of a solution containing N. ellipsosporum on gate region of an exemplary fabricated FET biosensor for different DC gate voltages of 0 V, 1 V, and 2 V, consistent with one or more exemplary embodiments of the present disclosure.

In order to investigate selectivity of an exemplary FET biosensor, impedance change during bacteria cell loading was analyzed for the different bacteria cells and results are shown in FIGS. 9A-9C. FIG. 9A shows real part of source-drain impedance versus frequency of an applied source-drain AC voltage while placing solutions containing *E. coli* (curve 902), *S. platensis* (curve 904), *N. ellipsosporum* (curve 906), and *A. aceti* (curve 908) on gate region of an exemplary fabricated FET biosensor, consistent with one or more exemplary embodiments of the present disclosure. As may be seen, impedance spectra for different cells are different.

As described in an exemplary embodiment of the present disclosure, gate voltage may affect source-drain impedance spectra. For example, FIG. 9B shows real part of source-drain impedance versus frequency of an applied source-drain AC voltage in the presence of a solution containing *E. coli* on gate region of an exemplary fabricated FET biosensor for different DC gate voltages of 0 V (curve 910), 1 V (curve 912), and 2 V (curve 914), consistent with one or more exemplary embodiments of the present disclosure.

Furthermore, FIG. 9C shows real part of source-drain impedance versus frequency of an applied source-drain AC voltage in the presence of a solution containing N. ellipsosporum on gate region of an exemplary fabricated FET biosensor for different DC gate voltages of 0 V (curve 916), 1 V (curve 918), and 2 V (curve 920), consistent with one or more exemplary embodiments of the present disclosure. It may be seen that in case of E. coli (FIG. 9B) increasing gate voltage leads to an increment in a peak intensity of impedance spectra. In contrast, source-drain impedance decreases by increasing gate voltage in case of N. ellipsosporum (FIG. 9C).

Figure 10A:
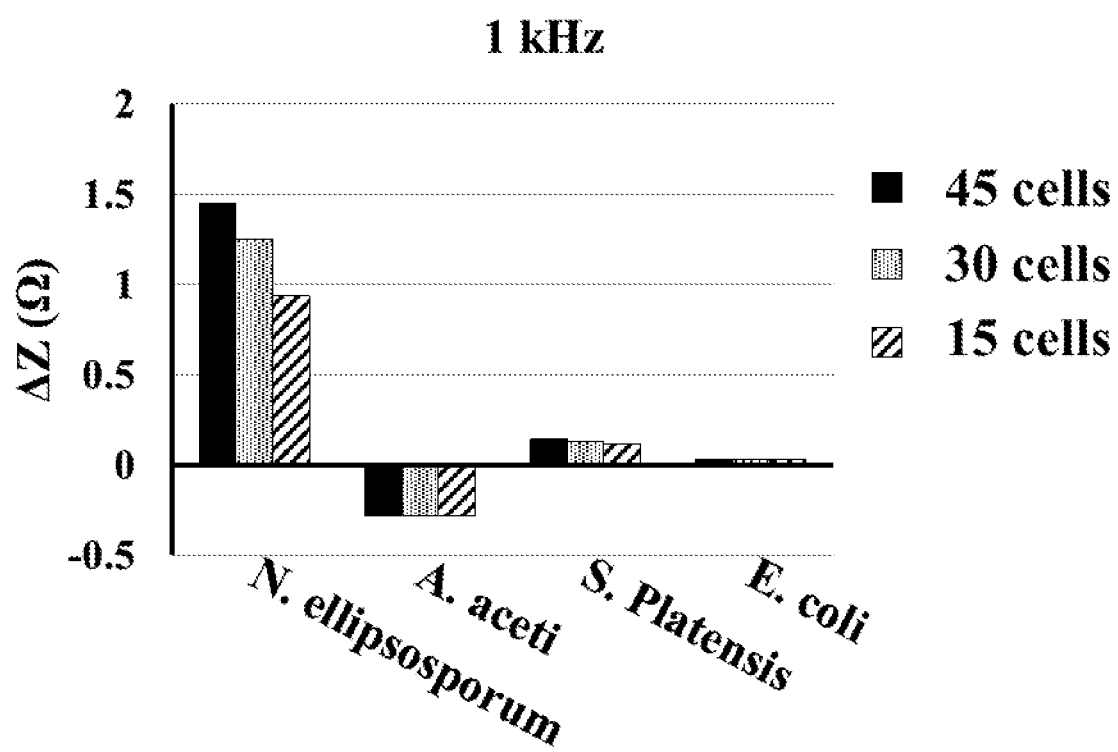
FIG. 10A shows impedance changes at a frequency of 1 MHz for different bacteria cells with different concentrations with 15, 30 and 45 cell numbers, consistent with one or more exemplary embodiments of the present disclosure.
Figure 10B:
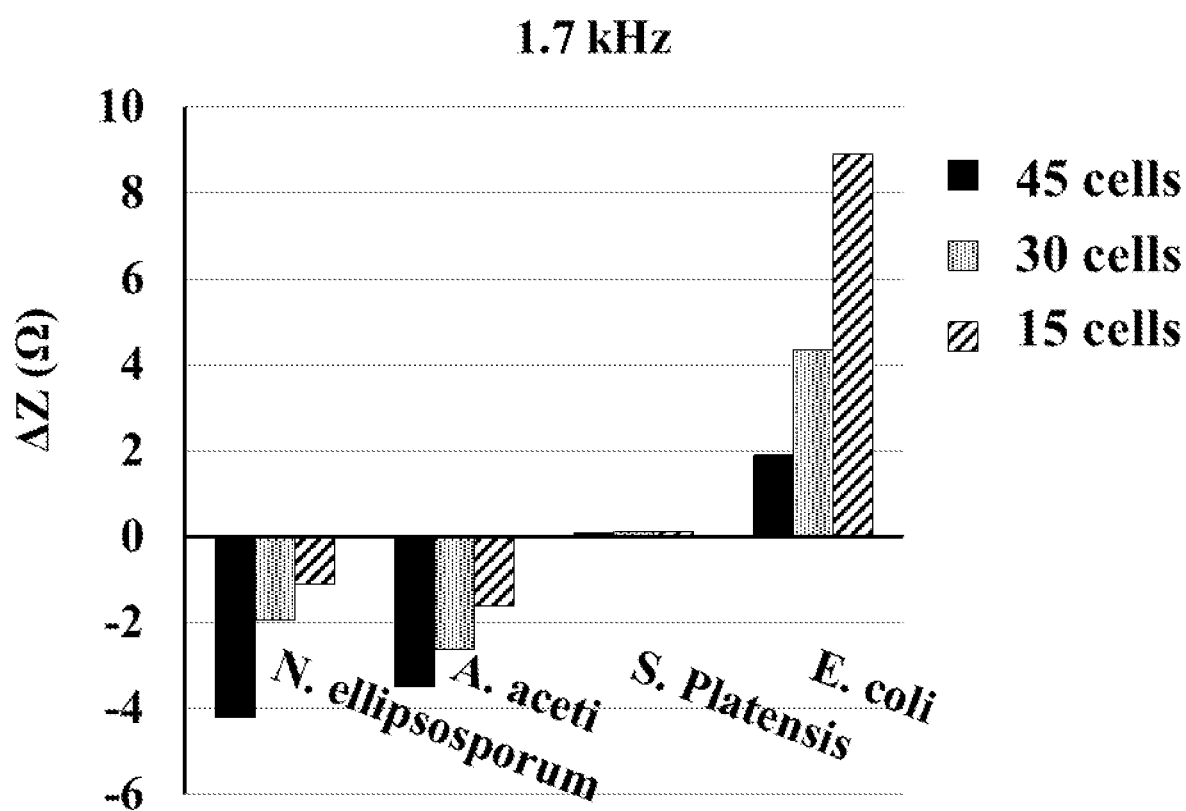
FIG. 10B shows impedance changes at a peak frequency ($f_m$) of 1.7 MHz for different bacteria cells with different concentrations with 15, 30 and 45 cell numbers, consistent with one or more exemplary embodiments of the present disclosure.
Figure 10C:
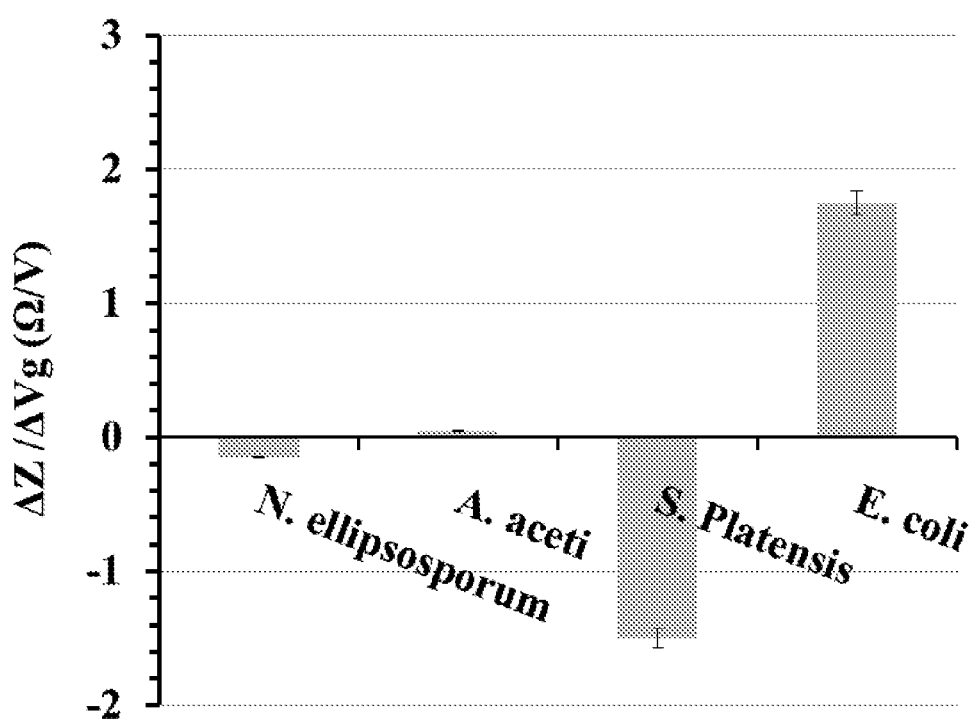
FIG. 10C shows collectively summarized gate DC voltage effects, consistent with one or more exemplary embodiments of the present disclosure.

FIGS. 8A-8D and FIGS. 9B and 9C show that in frequency of about 1.7 MHz, bacteria have different electrostatic behavior and have a different response to gate voltage. There is a peak in impedance at frequency 1.7 MHz, as an example of $f_m$ described herein above, and sensitivity is maximum at this frequency. Therefore, this frequency may be picked for further analyzing electrical behavior of bacteria by exemplary FET biosensor. On the other hand, it can be seen that around frequency of 1 MHz, no special response is observed. Detailed analyses of results are presented in FIGS. 10A and 10B. FIG. 10A shows impedance changes at a frequency of 1 MHz for different bacteria cells with different concentrations with 15, 30 and 45 cell numbers, consistent with one or more exemplary embodiments of the present disclosure. Furthermore, FIG. 10B shows impedance changes at a peak frequency ($f_m$) of 1.7 MHz for different bacteria cells with different concentrations with 15, 30 and 45 cell numbers, consistent with one or more exemplary embodiments of the present disclosure. As shown in FIG. 10A, impedance change at 1.7 MHz for E. coli is not significant. But it is considerable for N. ellipsosporum and A. aceti. It should be noted that impedance change for A. aceti is negative. According to results of FIG. 10B, impedance change at 1.7 MHz for S. platensis is not significant. Also, in contrast to results of FIG. 10A, impedance change for E. coli at 1.7 MHz is significant and impedance change for N. ellipsosporum is negative. Such contrast in results of impedance change may lead to selectively detect different cells. Further distinctive results that can improve selectivity of an exemplary FET biosensor, are represented in FIGS. 9B and 9C and furthermore in FIG. 10C. FIG. 10C shows collectively summarized gate DC voltage effects. FIG. 10C shows an exemplary parameter g=ΔZreal/ΔVg for different bacteria species at frequency of 1.7 MHz, consistent with one or more exemplary embodiments of the present disclosure. It may be seen that ΔZreal/ΔVg for N. ellipsosporum and A. aceti are very small, while it is large negative for S. platensis and large positive for E. coli. Such different behavior of exemplary FET biosensor electrical parameters in the presence of different bacteria species, such as ΔZreal/ΔVg, improves exemplary FET biosensor selectivity for bacteria sensing.

Figure 11A:
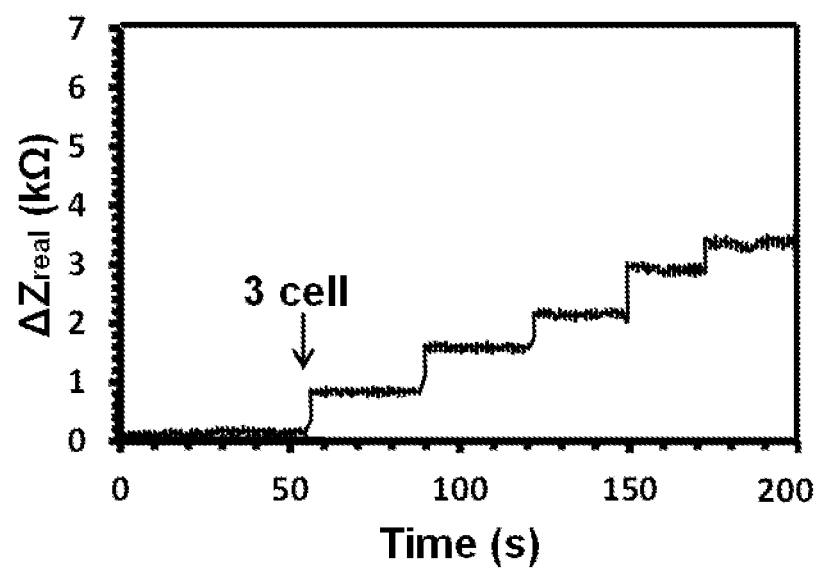
FIG. 11A shows real time measurement of source-drain impedance at 1.7 MHz and applied DC gate voltage of 0 V for step-by-step E. coli loading, consistent with one or more exemplary embodiments of the present disclosure.
Figure 11B:
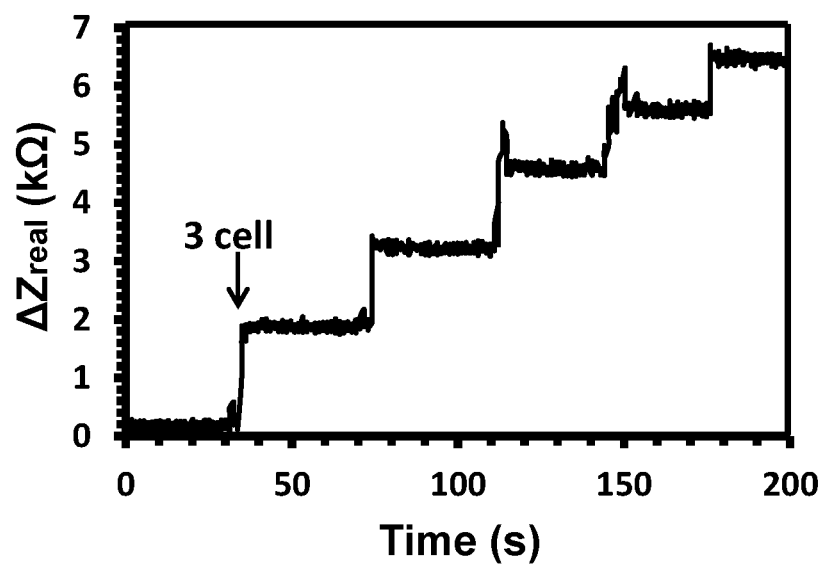
FIG. 11B shows real time measurement of source-drain impedance at 1.7 MHz and applied DC gate voltage of 2 V for step-by-step E. coli loading, consistent with one or more exemplary embodiments of the present disclosure.
Figure 11C:
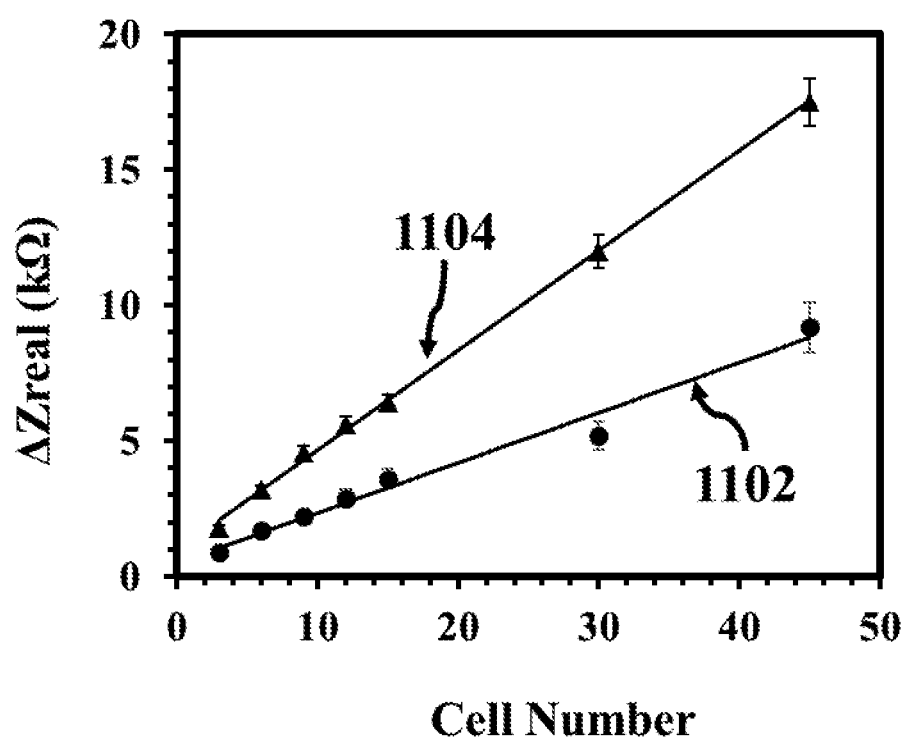
FIG. 11C shows impedance change versus cell number at 1.7 MHz and applied DC gate voltages of 0 V and 2 V for step-by-step E. coli loading on an exemplary FET biosensor, consistent with one or more exemplary embodiments of the present disclosure.

Based on results of FIGS. 9B and 9C and FIGS. 10A-10C, a distinguished source-drain voltage with a selected frequency and gate voltage may be set for an exemplary FET biosensor for selective detection of bacteria. Using such setting parameter, rapid and selective detection of bacteria may be realized. FIGS. 11A-11C show real time measurement of sensitivity of an exemplary FET biosensor. Real time measurement of source-drain impedance at an exemplary $f_m$ of 1.7 MHz and applied gate voltage of 0 V and 2V for step-by-step E. coli loading is shown in FIGS. 11A and 11B, respectively. Sensitivity of an exemplary FET biosensor in these set points is negligible for S. platensis and is small negative for A. aceti and N. ellipsosporum. FIG. 11C shows impedance change versus cell number at 1.7 MHz and applied DC gate voltages of 0 V (diagram 1102) and 2 V (diagram 1104) for step-by-step E. coli loading on an exemplary FET biosensor, consistent with one or more exemplary embodiments of the present disclosure. Impedance change versus cell number in FIG. 11C shows a linear response of an exemplary FET biosensor. Applying gate voltage increases sensitivity of an exemplary FET biosensor. An exemplary highest sensitivity obtained is 184 Ω/cell which may lead to a high Level of Detection (LOD) without using an antibody as a bioreceptor.

Referring back to FIGS. 8A-8E, FIGS. 9A-9C, and FIGS. 10A-10C, it may be seen that physical properties of bacteria may affect electrical characteristics of an exemplary FET biosensor. In detail, cell impedance, which depends on shape and wall charges of cells, may affect source-drain current of exemplary FET biosensor. For example, a presence of some bacteria on gate region of exemplary FET biosensor may increase source-drain current at a specific frequency (i.e., $f_m$) and some others may decrease the current. Additionally, gate effect on source-drain current of exemplary FET biosensor at an exemplary $f_m$ for different bacteria may be respectively different. Some electrical parameters may be defined that may have positive sign for some bacteria and negative sign for others. It means that frequency dependent electrical parameters of exemplary FET biosensor may be sensitive to shape, charge, and other physical properties of bacteria. Accordingly, a distinguished source-drain voltage with a selected frequency and DC gate voltage may be set for selectively detection of a target bacteria cell utilizing an exemplary FET biosensor similar to FET biosensor 102. Using a specific parameter and proper set points, rapid and selective detection of bacteria may be realized. A reference database based on measurements of an exemplary set of defined electrical parameters (e.g., $\Delta Z_{1m}$, $f_m$, and g) of an exemplary FET biosensor exposed to a plurality of species of bacteria may be generated for detection and quantification a species of bacteria in an exemplary suspected sample solution to have bacteria therein.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments. This is for purposes of streamlining the disclosure, and is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

While various embodiments have been described, the description is intended to be exemplary, rather than limiting and it will be apparent to those of ordinary skill in the art that many more embodiments and embodiments are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. A method for detecting a species of bacteria in a sample solution, comprising:
    putting the sample solution in contact with an array of zinc oxide (ZnO) nanorods grown on a gate region of a field effect transistor (FET) biosensor, the sample solution comprising a solution suspected to contain bacteria;
    applying an alternating current (AC) voltage at a set of frequencies of 500 Hz to 2 MHz between a source electrode within a source region of the FET biosensor and a drain electrode within a drain region of the FET biosensor;
    applying a first direct current (DC) voltage of $V_1$ to the sample solution on the gate region;
    measuring a first set of electrical impedance values ($Z_1$) between the source region and the drain region responsive to the applied AC voltage and the applied $V_1$, the $Z_1$ comprising a first set of real part magnitude of electrical impedance respective to the set of frequencies;
    calculating, utilizing one or more processors, a first impedance difference set ($\Delta Z_1$) by calculating a difference between each electrical impedance value of the $Z_1$ measured at a respective frequency ($f_i$) of the set of frequencies and a respective electrical impedance value of a first initial set of electrical impedance values ($Z_1^0$) associated with a bacteria-free reference solution measured at the same frequency $f_i$, calculating each first impedance difference being done using a relation defined by:

$$(\Delta Z_1)f_i = (Z_1)f_i - (Z_1^0)f_i;$$

determining, utilizing the one or more processors, bacteria indicative factors, comprising:
        detecting a first impedance difference peak value ($\Delta Z_{1m}$) of the $\Delta Z_1$; and
        determining a peak frequency ($f_m$) of the set of frequencies respective to the $\Delta Z_{1m}$; and
    detecting a presence of a first species of bacteria in the sample solution based on the bacteria indicative factors.

2. The method of claim 1, further comprising measuring the first initial set of electrical impedance values ($Z_1^0$), comprising:
    putting the bacteria-free reference solution on the gate region of the FET biosensor in contact with the array of ZnO nanorods;
    applying the AC voltage between the source electrode and the drain electrode at the set of frequencies;
    applying the first DC voltage of $V_1$ to the bacteria-free reference solution on the gate region; and
    measuring a set of real part magnitude of electrical impedance between the source region and the drain region versus the set of frequencies.

3. The method of claim 1, wherein detecting the presence of the first species of bacteria in the sample solution comprises detecting the presence of the first species of bacteria in the sample solution based on at least one of a range of the $\Delta Z_1$, a value of the $f_m$, a value of the $\Delta Z_{1m}$, a sign of a plurality values of the $\Delta Z_1$, and combinations thereof, detecting the presence of the first species of bacteria in the sample solution comprising detecting a first set of conditions, the first set of conditions comprising at least one of the calculated $\Delta Z_{1m}$ being within a range of first reference impedance difference peak values ($\Delta Z_{1rm}$) associated with the first species of bacteria, the determined $f_m$ being equal to a reference peak frequency ($f_{rm}$) associated with the first species of bacteria, sign of the plurality values of the $\Delta Z_1$ being the same with sign of a plurality of at least one of first reference impedance difference sets ($\Delta Z_{1r}$) associated with the first species of bacteria, and combinations thereof.

4. The method of claim 3, wherein determining the $f_m$ comprises detecting the $f_m$ being equal to a frequency of 1.7 MHz respective to the $\Delta Z_{1m}$.

5. The method of claim 4, wherein detecting the presence of the first species of bacteria in the sample solution comprises detecting a presence of helical bacteria in the sample solution responsive to a constant value for a plurality of the $\Delta Z_1$ respective to a plurality of frequencies of the set of frequencies more than 1.7 MHz.

6. The method of claim 4, wherein detecting the presence of the first species of bacteria in the sample solution comprises detecting a presence of bacteria with longitudinal colonic growth in the sample solution responsive to a negative sign of a plurality values of the $\Delta Z_1$ respective to a plurality of frequencies of the set of frequencies more than 1.7 MHz.

7. The method of claim 4, wherein detecting the presence of the first species of bacteria in the sample solution comprises detecting a presence of at least one of spherical bacteria with non-longitudinal growth, rod-shaped bacteria with non-longitudinal growth, and combinations thereof in the sample solution responsive to a positive sign of a plurality values of the $\Delta Z_1$ respective to a plurality of frequencies of the set of frequencies more than 1.7 MHz.

8. The method of claim 3, further comprising generating a reference dataset for a plurality of bacteria species by generating a plurality of first reference impedance difference sets ($\Delta Z_{1r}$), a plurality of reference impedance difference peak values ($\Delta Z_{1rm}$) ranges, and a plurality of reference peak frequencies ($f_{rm}$) associated with the plurality of bacteria species, comprising:
preparing a set of reference solutions containing a respective set of concentrations of each bacteria species of the plurality of the bacteria species; and
determining the $\Delta Z_{1r}$, the $\Delta Z_{rm}$, and the $f_{rm}$ for each bacteria species, comprising:
putting each respective reference solution on the gate region of the FET biosensor in contact with the array of ZnO nanorods;
applying the AC voltage with the set of frequencies between the source electrode and the drain electrode while applying the $V_1$ to the gate region;
measuring a respective first reference set of electrical impedance values ($Z_{1r}$) comprising a first reference set of real part magnitude of electrical impedance between the source region and the drain region respective to the set of frequencies;
calculating a respective first reference impedance difference set ($\Delta Z_{1r}$) by calculating a difference between each electrical impedance value of the $Z_{1r}$ and a respective electrical impedance value of the first initial set $Z_1^0$ using a relation defined by:

$(\Delta Z_{1r})f_i = (Z_{1r})f_i - (Z_1^0)f_i;$ detecting a respective first reference peak value $\Delta Z_{1rm}$ of the first reference impedance difference set $\Delta Z_{1r}$; and
determining a reference peak frequency ($f_{rm}$) of the set of frequencies respective to the $\Delta Z_{1rm}$.

9. The method of claim 3, further comprising measuring a change in impedance difference peak value responsive to a change in the applied DC voltage, comprising:
applying a second DC voltage of $V_2$ to the sample solution on the gate region;
measuring a second set of electrical impedance values ($Z_2$) between the source region and the drain region responsive to the applied AC voltage and the applied $V_2$, the $Z_2$ comprising a second set of real part magnitude of electrical impedance respective to the set of frequencies;
calculating a second impedance difference set ($\Delta Z_2$) by calculating a difference between each electrical impedance value of the $Z_2$ measured at a respective frequency ($f_i$) of the set of frequencies and a respective electrical impedance value of a second initial set of electrical impedance values ($Z_2^0$) measured at the same frequency $f_i$, calculating each second impedance difference being done using a relation defined by:

$(\Delta Z_2)f_i = (Z_2)f_i - (Z_2^0)f_i;$ and determining a second impedance difference peak value ($\Delta Z_{2m}$) of the $\Delta Z_2$ respective to the peak frequency ($f_m$).

10. The method of claim 9, wherein:
applying the first DC voltage of $V_1$ to the sample solution comprises applying a DC voltage of 1 V to the sample solution; and
applying the second DC voltage of $V_2$ to the sample solution comprises applying a DC voltage of 2 V to the sample solution.

11. The method of claim 9, further comprising measuring the second initial set of electrical impedance values ($Z_2^0$), comprising:
putting the bacteria-free reference solution on the gate region of the FET biosensor in contact with the array of ZnO nanorods;
applying the AC voltage between the source electrode and the drain electrode within the set of frequencies;
applying the second DC voltage of $V_2$ to the bacteria-free reference solution on the gate region; and
measuring a set of real part magnitude of electrical impedance between the source region and the drain region versus the set of frequencies.

12. The method of claim 9, wherein determining the bacteria indicative factors further comprises determining a parameter g comprising an indicator of the change in impedance difference peak value responsive to the change in the applied DC voltage, determining the parameter g comprising calculating the parameter g using a relation defined by:

$$g = \frac{\Delta Z_{2m} - \Delta Z_{1m}}{V_2 - V_1}.$$

13. The method of claim 12, wherein detecting the presence of the first species of bacteria in the sample solution further comprises detecting sign of the parameter g being the same with sign of a reference g ($g_r$) range associated with the first species of bacteria.

14. The method of claim 13, wherein detecting the presence of the first species of bacteria in the sample solution comprises detecting a presence of helical bacteria in the sample solution responsive to detecting a second set of conditions, the second set of conditions comprising:
the determined $f_m$ being equal to a frequency of 1.7 MHz;
a constant value for a plurality of the $\Delta Z_1$ respective to a plurality of frequencies more than 1.7 MHz; and
a negative sign of the calculated parameter g.

15. The method of claim 13, further comprising generating a reference dataset for a plurality of bacteria species by generating a plurality of first reference impedance difference sets ($\Delta Z_{1r}$), a plurality of first reference impedance difference peak values ($\Delta Z_{1rm}$) ranges, a plurality of reference g ($g_r$) ranges, and a plurality of a reference peak frequencies ($f_{rm}$) associated with the plurality of bacteria species, comprising:
preparing a set of reference solutions containing a respective set of concentrations of each bacteria species of the plurality of the bacteria species; and
determining $\Delta Z_{1r}$, $\Delta Z_{1rm}$, $g_r$ range, and $f_{rm}$ for each bacteria species, comprising:

putting each respective reference solution on the gate region of the FET biosensor in contact with the array of ZnO nanorods;
applying the AC voltage with the set of frequencies between the source electrode and the drain electrode while applying the $V_1$ to the gate region;
measuring a respective first reference set of electrical impedance values ($Z_{1r}$) comprising a first reference set of real part magnitude of electrical impedance between the source region and the drain region respective to the set of frequencies;
calculating a respective first reference impedance difference set ($\Delta Z_{1r}$) by calculating a difference between each electrical impedance value of the $Z_{1r}$ and a respective electrical impedance value of the initial set $Z_1^0$ using a relation defined by:

$$(\Delta Z_{1r})f_i = (Z_{1r})f_i - (Z_1^0)f_i;$$

detecting a respective first reference peak value $\Delta Z_{1rm}$ of the first reference impedance difference set $\Delta Z_{1r}$;
determining a reference peak frequency ($f_{rm}$) of the set of frequencies respective to the $\Delta Z_{1rm}$; and
measuring a change in reference impedance difference peak value responsive to applying the $V_2$ DC voltage to the gate region by calculating a parameter $g_r$ using a relation defined by:

$$g_r = \frac{\Delta Z_{2rm} - \Delta Z_{1rm}}{V_2 - V_1},$$

wherein the $\Delta Z_2$, comprises a second reference impedance difference peak value at the $f_{rm}$ of a second reference impedance difference set ($\Delta Z_{2r}$) measured responsive to the applied $V_2$.

16. The method of claim 15, further comprising determining an amount of the first species of bacteria in the sample solution by determining the amount of the first species of bacteria in the sample solution equal to a $n^{th}$ concentration ($C_n$) of the set of concentrations of the first species of bacteria associated with a first determined $f_{rm}$, a respective $n^{th}$ first reference impedance difference set ($\Delta Z_{1r}$)$_n$, and a respective $n^{th}$ first $g_r$ responsive to detecting a third set of conditions, the third set of conditions comprising:
the determined $f_m$ being equal to the first determined $f_{rm}$ associated with the first species of bacteria;
the calculated $\Delta Z_{1m}$ being equal to a $(\Delta Z_{1rm})_n$ value associated with the $C_n$ of the set of concentrations of the first species of bacteria; and
the calculated g being equal to the $n^{th}$ first $g_r$ value associated with the $C_n$ of the set of concentrations of the first species of bacteria.

17. The method of claim 1, further comprising fabricating the FET biosensor, comprising:
removing impurities from a semiconductor substrate by cleaning the semi conductor substrate;
forming a dielectric layer on the semiconductor substrate;
forming the source region and the drain region on the semiconductor substrate by patterning and etching the dielectric layer in the source region and the drain region;
increasing electrical conductivity of the source region and the drain region via changing semiconductor characteristics of the source region and the drain region by doping the source region and the drain region;
growing the array of ZnO nanorods on the gate region on the dielectric layer between the source region and the drain region; and
forming the source electrode and the drain electrode by depositing a first electrical conductive layer on the doped source region and a second electrical conductive layer on the doped drain region.

18. The method of claim 1, further comprising differentiating a presence of gram-positive bacteria and gram-negative bacteria in the sample solution, comprising:
exposing the sample solution on the gate region to blue light irradiation;
applying the AC voltage with the set of frequencies of 500 Hz to 2 MHz between the source electrode and the drain electrode;
applying the first DC voltage of $V_1$ to the sample solution on the gate region;
measuring a third set of electrical impedance values ($Z_3$) between the source region and the drain region responsive to the applied AC voltage and the applied $V_1$ in the presence of blue light radiation, the $Z_3$ comprising a third set of real part magnitude of electrical impedance respective to the set of frequencies;
calculating a third impedance difference set ($\Delta Z_3$) by calculating a difference between each electrical impedance value of the $Z_3$ measured at a respective frequency ($f_i$) of the set of frequencies and a respective electrical impedance value of the initial set of electrical impedance values ($Z_1^0$) measured at the same frequency $f_i$, calculating each third impedance difference being done using a relation defined by:

$$(\Delta Z_3)f_i = (Z_3)f_i - (Z_1^0)f_i;$$

detecting a third impedance difference peak value ($\Delta Z_{3m}$) of the $\Delta Z_3$ respective to the peak frequency ($f_m$); and
differentiating the presence of gram-positive bacteria and gram-negative bacteria in the sample solution, comprising:
detecting a presence of gram-negative bacteria in the sample solution responsive to the calculated $\Delta Z_{1m}$ and $\Delta Z_{3m}$ having the same sign; or
detecting a presence of gram-positive bacteria in the sample solution responsive to the calculated $\Delta Z_{1m}$ and $\Delta Z_{3m}$ having opposite signs.

* * * * *